United States Patent
Shin et al.

(10) Patent No.: US 9,481,631 B2
(45) Date of Patent: *Nov. 1, 2016

(54) PHENOLIC HYDROXYL GROUP-CONTAINING COMPOUND, PHENOLIC HYDROXYL GROUP-CONTAINING COMPOSITION, (METH)ACRYLOYL GROUP-CONTAINING RESIN, CURABLE COMPOSITION, CURED PRODUCT THEREOF, AND RESIST MATERIAL

(71) Applicant: DIC Corporation, Tokyo (JP)

(72) Inventors: Dongmi Shin, Ichihara (JP); Tomoyuki Imada, Ichihara (JP); Takakazu Kage, Ichihara (JP)

(73) Assignee: DIC Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/443,702

(22) PCT Filed: Nov. 20, 2013

(86) PCT No.: PCT/JP2013/081265
§ 371 (c)(1),
(2) Date: May 19, 2015

(87) PCT Pub. No.: WO2014/084097
PCT Pub. Date: Jun. 5, 2014

(65) Prior Publication Data
US 2015/0274636 A1    Oct. 1, 2015

(30) Foreign Application Priority Data

Nov. 28, 2012    (JP) ................................ 2012-259742

(51) Int. Cl.
*C08L 69/00* (2006.01)
*C07C 69/54* (2006.01)
(Continued)

(52) U.S. Cl.
CPC .............. *C07C 69/54* (2013.01); *C08F 220/30* (2013.01); *C08F 283/06* (2013.01);
(Continued)

(58) Field of Classification Search
CPC ....... C07C 69/54; C07C 37/20; C07C 39/16; C07C 67/14
See application file for complete search history.

(56) References Cited

FOREIGN PATENT DOCUMENTS

| JP | 09-157340 A | 6/1997 | |
|---|---|---|---|
| JP | 2004054002 | * 2/2004 | ............. G03C 1/498 |

*Primary Examiner* — Shane Fang
(74) *Attorney, Agent, or Firm* — Locke Lord LLP

(57) ABSTRACT

The present invention provides a (meth)acryloyl group-containing resin having excellent heat resistance and a phenolic hydroxyl group-containing compound used as a raw material of the resin. A phenolic hydroxyl group-containing compound has a molecular structure represented by general formula (1) below [in the formula, $R^1$, $R^2$, and $R^3$ are each independently an alkyl group having 1 to 8 carbon atoms, m and n are each independently an integer of 1 to 4, p is an integer of 0 to 4, V is a hydrogen atom, a (meth)acryloyloxy group, or a hydroxyl group, and W, X, and Y are each independently a (meth)acryloyloxy group or a hydroxyl group], wherein at least one of V, W, X, and Y is a hydroxyl group, and at least one of V, W, X, and Y is a (meth)acryloyloxy group.

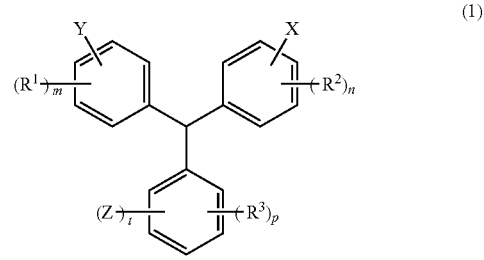

9 Claims, 1 Drawing Sheet

(51) Int. Cl.
  *C08G 8/30*   (2006.01)
  *G03F 7/027*  (2006.01)
  *C08F 220/30* (2006.01)
  *C09D 133/08* (2006.01)
  *C08G 8/04*   (2006.01)
  *C09D 161/14* (2006.01)
  *C08F 299/02* (2006.01)
  *C08F 283/06* (2006.01)

(52) U.S. Cl.
  CPC ............ *C08F 299/024* (2013.01); *C08G 8/04* (2013.01); *C08G 8/30* (2013.01); *C09D 133/08* (2013.01); *C09D 161/14* (2013.01); *G03F 7/027* (2013.01); *C08F 2220/302* (2013.01)

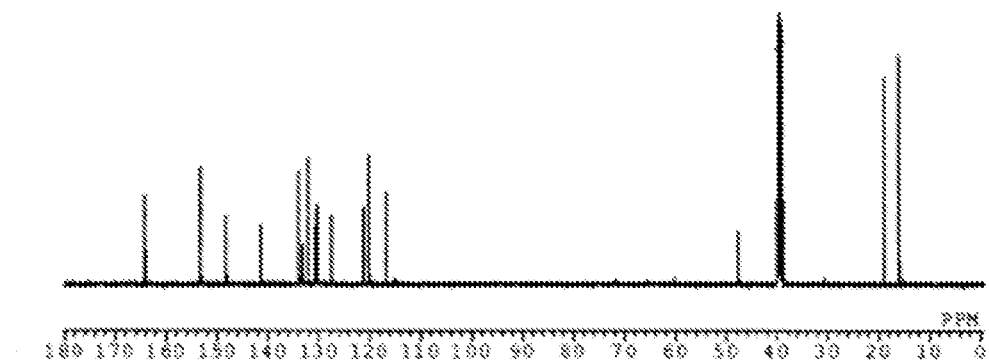

PHENOLIC HYDROXYL GROUP-CONTAINING COMPOUND, PHENOLIC HYDROXYL GROUP-CONTAINING COMPOSITION, (METH)ACRYLOYL GROUP-CONTAINING RESIN, CURABLE COMPOSITION, CURED PRODUCT THEREOF, AND RESIST MATERIAL

TECHNICAL FIELD

The present invention relates to a (meth)acryloyl group-containing resin which produces a cured product having excellent heat resistance, a phenolic hydroxyl group-containing compound used as a raw material of the resin, a curable composition, a cured product thereof, and a resist material.

BACKGROUND ART

Technology of electronic apparatuses has recently been significantly developed, and increases in density and performance improvement of integrated circuits have been rapidly advanced. Accordingly, printed circuit boards have also been further increased in density and wiring density and developed in surface mounting of components, and thus higher accuracy and performance than ever before have been required. In order to comply with the higher densities and higher performance of integrated circuits, performance improvement of solder resist used as a main material for integrated circuits has been investigated. However, build-up substrates having fine wiring therein have the problem of causing cracking called a "popcorn phenomenon" at an interface between a solder resist and an encapsulating resin, and solder resist having higher heat resistance is required.

With increases in integration of integrated circuits, a nanoimprint method attracts attention as a method for superfine patterning with a line width of 20 nm or less. The nanoimprint method is roughly divided into a thermal nanoimprint method and an optical nanoimprint method. The thermal nanoimprint method includes pressing a mold on a polymer resin softened by heating to a temperature equal to or higher than the glass transition temperature and then releasing the mold after cooling to transfer a fine structure to a resin on a substrate, and thus the thermal nanoimprint method can form a nano-pattern at a relatively low cost and is expected to be applied to various fields. However, the thermal nanoimprint method requires softening of the polymer resin by heating and thus has difficulty in using a polymer resin having a high glass transition temperature and thus has difficulty in application to the electric/electronic field in which higher heat resistance has been required in recent years.

On the other hand, the optical nanoimprint method including optically curing a composition by light irradiation does not require heating of a molding material to which a pattern is transferred during pressing and is capable of imprint at room temperature. Light-curable resins applied to optical nanoimprint includes a radical polymerization type, an ionic polymerization type, and a hybrid type of the two types, and any type of curable resin composition can be used in nanoimprint application. However, a radical polymerization-type light-curable composition is widely investigated because of its wide range of selection of materials.

When in addition to the high-integration integrated circuit, a thin-film transistor of a liquid crystal display, a protective film of a liquid crystal color filter, a spacer, or a permanent film for application to fine processing of members of other liquid crystal display devices is formed by the nanoimprint method, a nanoimprint material capable of achieving high mechanical characteristics, transparency, light resistance, and heat resistance is required, and a material capable of producing a cured product having high heat resistance is particularly required.

For example, an epoxy (meth)acrylate resin having a biphenyl skeleton is known as a material which produces a cured product with high heat resistance and which is useful as a solder resist (refer to, for example, Patent Literature 1), but this resin does not have recently required high heat resistance.

CITATION LIST

Patent Literature

PTL 1: Japanese Unexamined Patent Application Publication No. 9-157340

SUMMARY OF INVENTION

Technical Problem

A problem to be solved by the present invention is to provide a (meth)acryloyl group-containing resin which is excellent in heat resistance and useful as a solder resist, a thin-film transistor, a protective film of a liquid crystal color filter, a spacer, and a permanent film for fine processing of members of other liquid crystal display devices, and also provide a phenolic hydroxyl group-containing composition used as a raw material of the resin, a curable composition, a cured product thereof, and a composition for a resist material.

Solution to Problem

As a result of repeated earnest research, the inventors found that a cured product of a (meth)acryloyl group-containing resin produced by reacting a phenolic hydroxyl group-containing composition having a triphenylmethane structure with an aldehyde compound has very high heat resistance, leading to the achievement of the present invention.

That is, the present invention provides a phenolic hydroxyl group-containing compound having a molecular structure represented by general formula (1) below,

[Chem. 1]

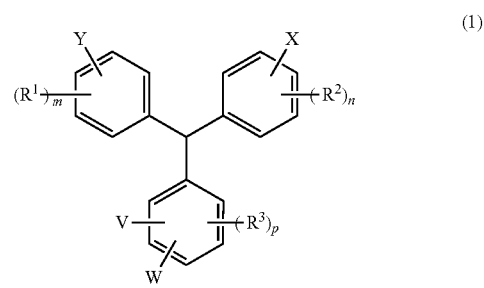

(1)

[in the formula, $R^1$, $R^2$, and $R^3$ are each independently an alkyl group having 1 to 8 carbon atoms, m and n are each independently an integer of 1 to 4, p is an integer of 0 to 4, V is a hydrogen atom, a (meth)acryloyloxy group, or a hydroxyl group, and W, X, and Y are each independently a (meth)acryloyloxy group or a hydroxyl group], wherein at least one of V, W, X, and Y is a hydroxyl group, and at least one of V, W, X, and Y is a (meth)acryloyloxy group.

Also, the present invention provides a phenolic hydroxyl group-containing composition containing a plurality of phenolic hydroxyl group-containing compounds represented by the general formula (1), wherein the average number of (meth)acryloyloxy groups per molecule is in a range of 0.5 to 2.5.

Further, the present invention provides a curable composition containing the phenolic hydroxyl group-containing compound.

Further, the present invention provides a (meth)acryloyl group-containing resin produced by reacting the phenolic hydroxyl group-containing composition with an aldehyde compound.

Further, the present invention provides a curable composition containing the (meth)acryloyl group-containing resin.

Further, the present invention provides a cured product produced by polymerizing the curable composition.

Further, the present invention provides a resist material including the curable composition.

Advantageous Effects of Invention

A cured product of a (meth)acryloyl group-containing resin of the present invention has a very high level of heat resistance. Therefore, the (meth)acryloyl group-containing resin of the present invention can be used as a material for solder resist required to have high heat resistance and a material for nanoimprint. Also, the (meth)acryloyl group-containing resin of the present invention has light curability and heat curability and is thus capable of optical molding and thermal molding, and thus can be used as a mold material for a thermal nanoimprint method. When an engineering plastic for electric/electronic materials which has a glass transition temperature (Tg) of over 200° C., such as polyphenylene ether (PPE) having high heat resistance, is used as a thermoplastic resin used for a resist in the thermal nanoimprint method, the softening temperature of the plastic is 300° C. or more, while the (meth)acryloyl group-containing resin of the present invention has very high heat resistance. Therefore, the (meth)acryloyl group-containing resin of the present invention can be used as a mold material.

Also, the (meth)acryloyl group-containing resin of the present invention has benzene rings at a high density and thus has a more rigid skeleton, and a cured product thereof has high heat resistance. Further, the cured product has high mechanical characteristics (shock resistance), high water resistance, and particularly high hardness due to the rigid skeleton. Therefore, the (meth)acryloyl group-containing resin of the present invention can be preferably used for a hard coat material for films of triacetyl cellulose (TAC) and the like which are used for polarizing plates of liquid crystal displays such as a television, a video camera, a computer, a cellular phone, and the like; a hard coat material for transparent protective films which protect the surfaces of various displays such as a liquid crystal display, a plasma display, an organic EL display, and the like; and a hard coat material for optical lenses.

BRIEF DESCRIPTION OF DRAWING

FIG. 1 is a chart of a 1H-NMR spectrum of a phenolic hydroxyl group-containing composition (1) produced in Synthesis Example 1.

DESCRIPTION OF EMBODIMENTS

A phenolic hydroxyl group-containing compound of the present invention has a molecular structure represented by general formula (1) below,

[Chem. 2]

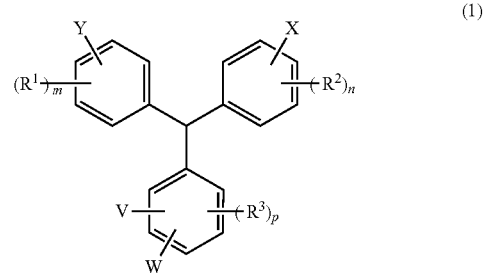

[in the formula, $R^1$, $R^2$, and $R^3$ are each independently an alkyl group having 1 to 8 carbon atoms, m and n are each independently an integer of 1 to 4, p is an integer of 0 to 4, V is a hydrogen atom, a (meth)acryloyloxy group, or a hydroxyl group, and W, X, and Y are each independently a (meth)acryloyloxy group or a hydroxyl group], wherein at least one of V, W, X, and Y is a hydroxyl group, and at least one of V, W, X, and Y is a (meth)acryloyloxy group.

In the general formula (1), $R^1$, $R^2$, and $R^3$ are each independently an alkyl group having 1 to 8 carbon atoms, and examples thereof include a methyl group, an ethyl group, a propyl group, an isopropyl group, a n-butyl group, a tert-butyl group, a pentyl group, a hexyl group, a heptyl group, an octyl group, and the like. These alkyl groups impart high heat resistance to the phenolic hydroxyl group-containing compound. Among these alkyl groups, a methyl group can impart high rigidity to molecules by suppressing molecular motion, provide a compound having high heat resistance, impart an electron donating property to a phenolic benzene nucleus, and is industrially easily available, and thus all of $R^1$, $R^2$, and $R^3$ are preferably methyl groups.

Also, in the general formula (1), m and n are each independently an integer of 1 to 4, and p is an integer of 0 to 4. In particular, for the reasons of high reactivity, the ease of reaction design, industrial easy availability of raw materials, etc., preferably, m and n are each independently 1 or 2, and p is an integer of 0 to 2.

In the general formula (1), V is a hydrogen atom, a (meth)acryloyloxy group, or a hydroxyl group, and W, X, and Y are each independently a (meth)acryloyloxy group or a hydroxyl group. With respect to a difference between an acryloyloxy group and a methacryloyloxy group, the acryloyloxy group can provide an acryl polymer having high adhesion to a substrate because of a high curing rate. On the other hand, the methacryloyloxy group can provide an acryl polymer having high adhesion to a substrate because of low curing shrinkage.

Examples of the phenolic hydroxyl group-containing compound represented by the general formula (1) include compounds having molecular structures represented by structural formulae (1-1) to (1-66) below.

[Chem. 3]
(1-1)
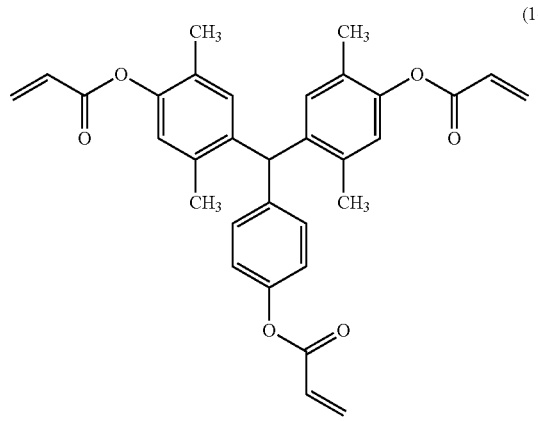
(1-2)
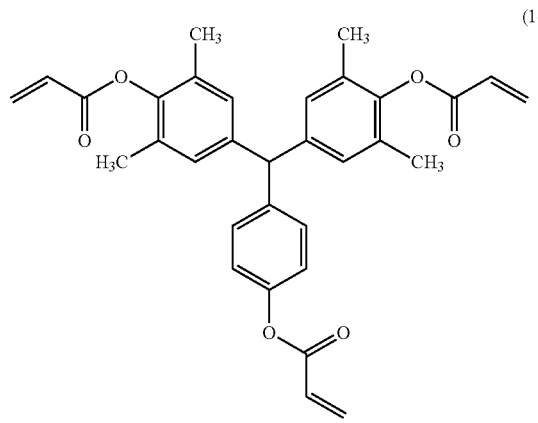
(1-3)
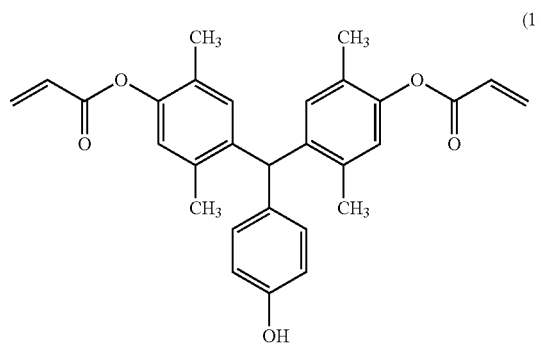
(1-4)
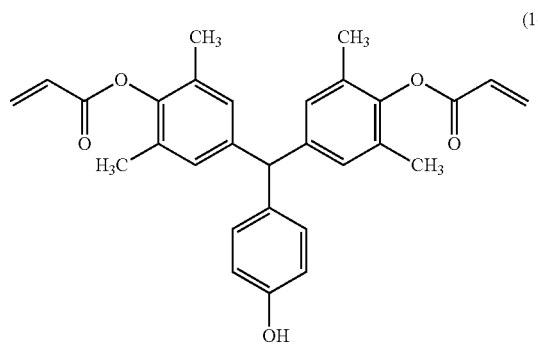
-continued
(1-5)
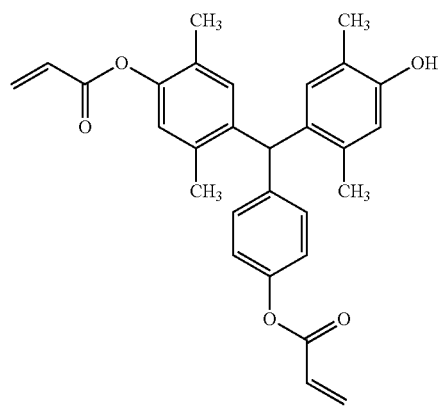
(1-6)
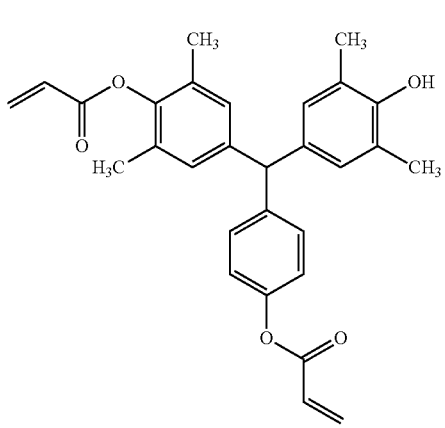
(1-7)
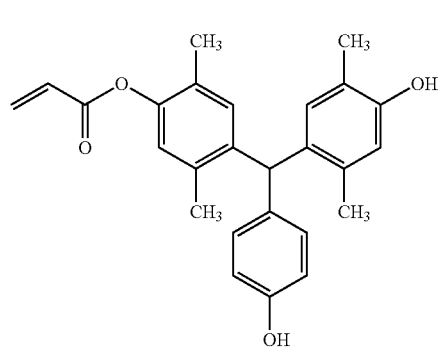
(1-8)
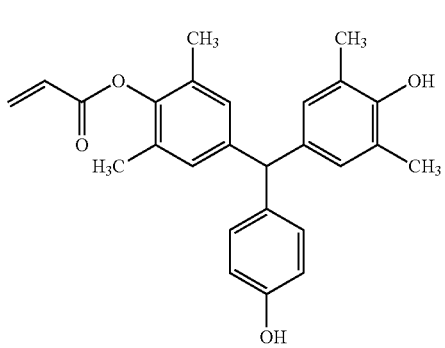

(1-9)
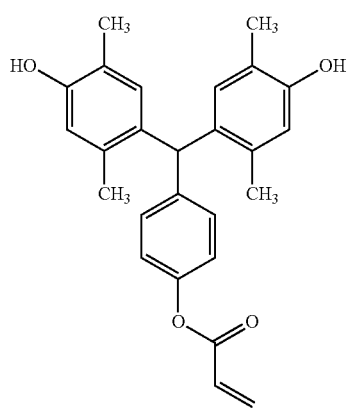
(1-10)
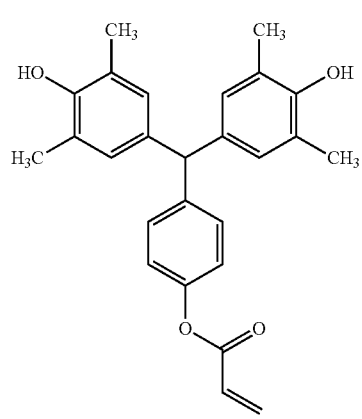
(1-11)
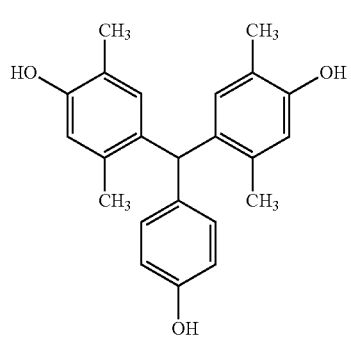
(1-12)
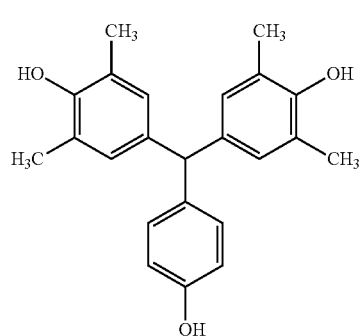
[Chem. 4]
(1-13)
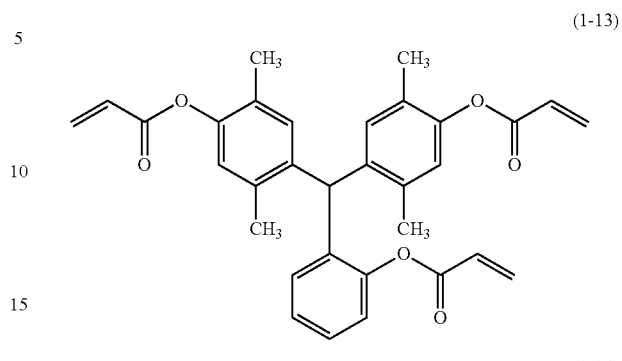
(1-14)
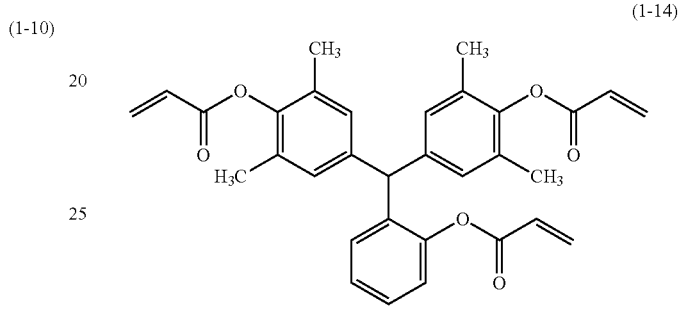
(1-15)
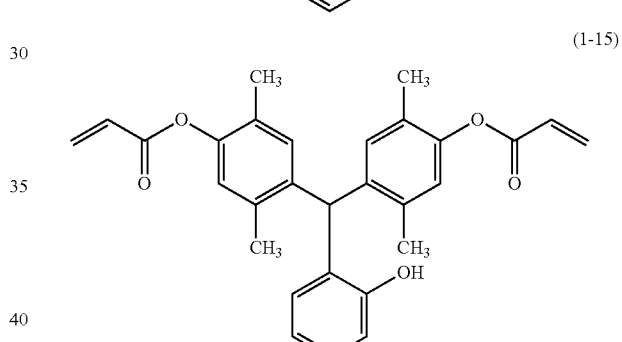
(1-16)
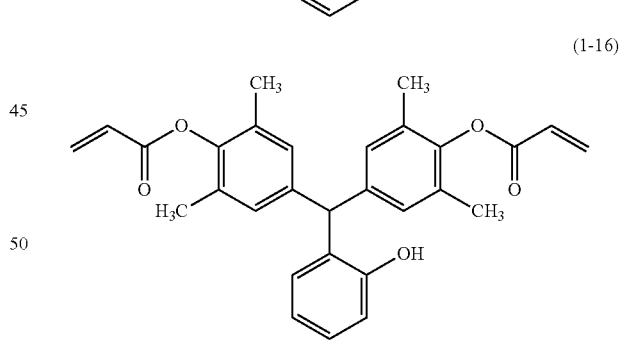
(1-17)
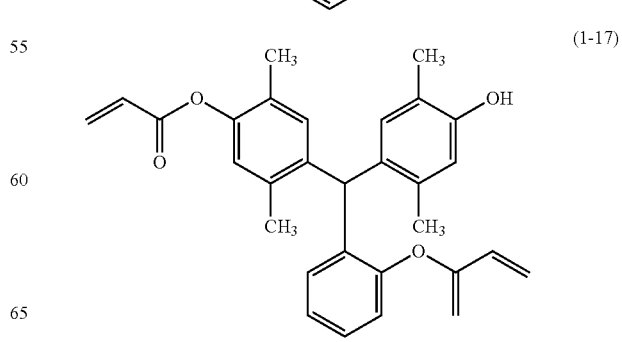

(1-18)
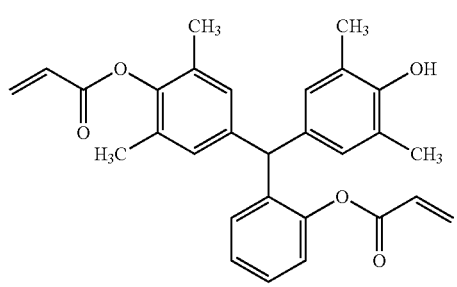
(1-19)
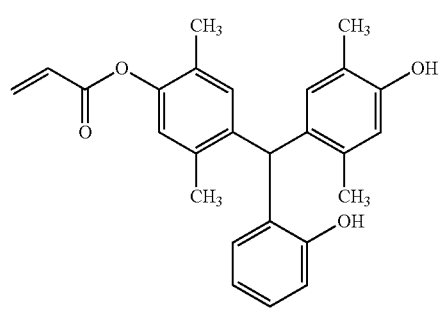
(1-20)
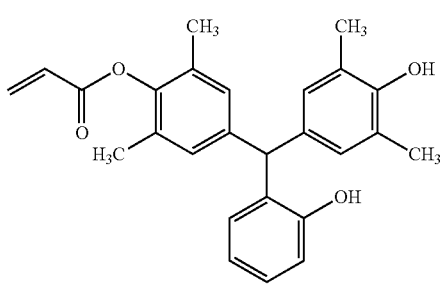
(1-21)
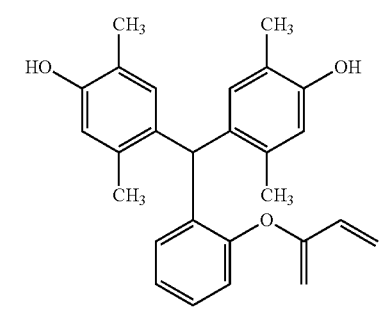
(1-22)
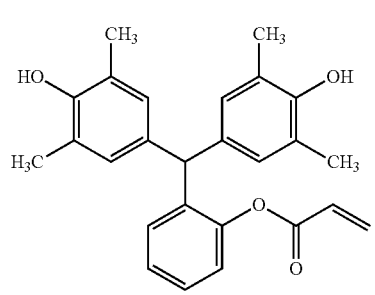
(1-23)
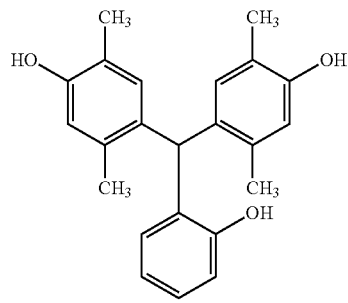
(1-24)
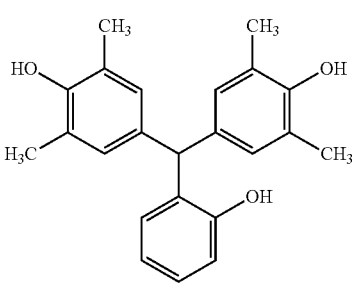
[Chem. 5]
(1-25)
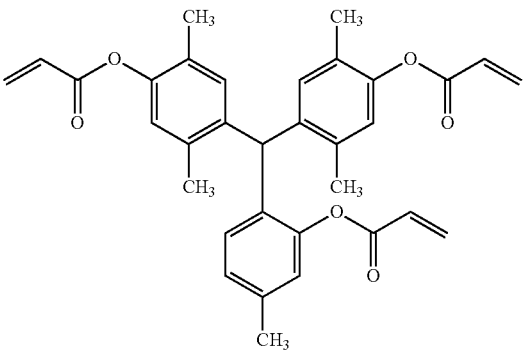
(1-26)
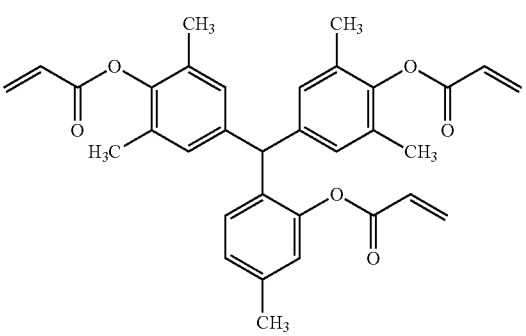

(1-27)
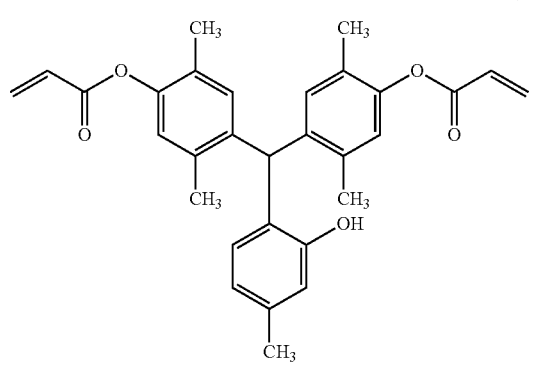
(1-28)
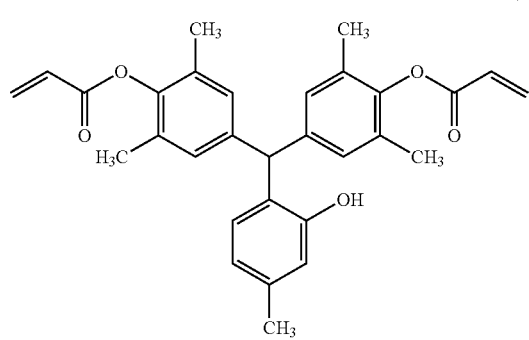
(1-29)
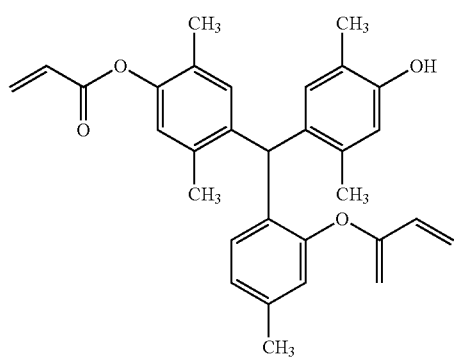
(1-30)
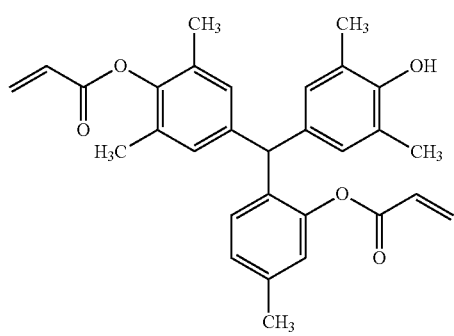
(1-31)
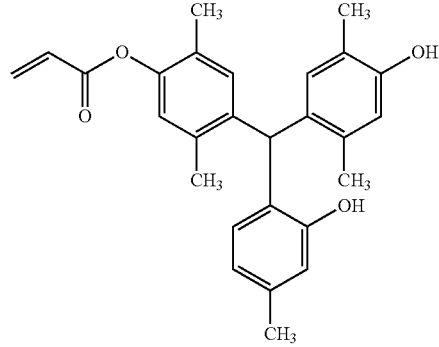
(1-32)
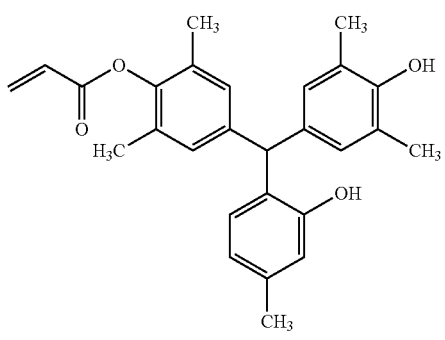
(1-33)
(1-34)
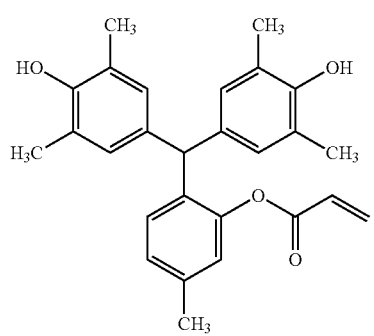

(1-35)
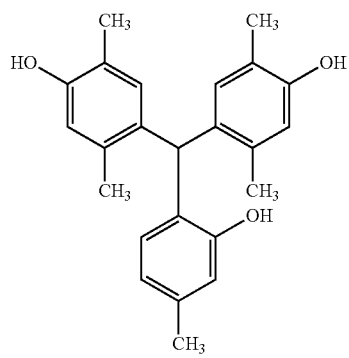
(1-36)
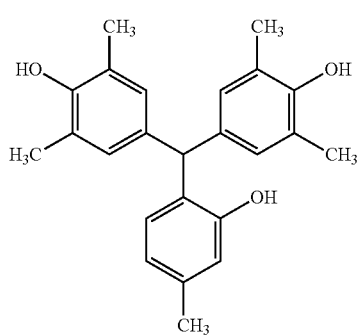
[Chem. 6]
(1-37)
(1-38)
(1-39)
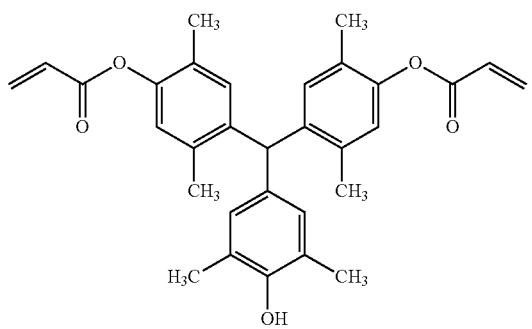
(1-40)
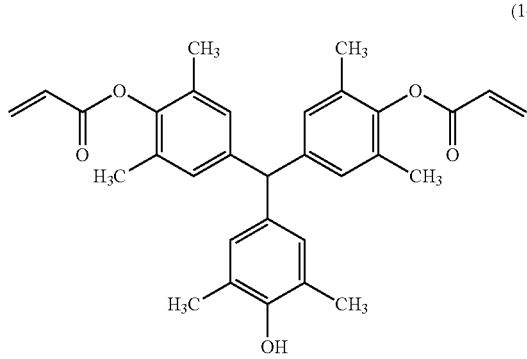
(1-41)
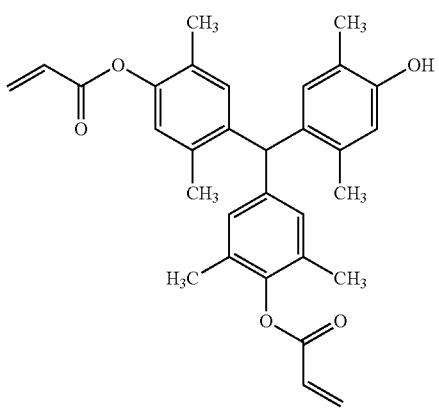
(1-42)
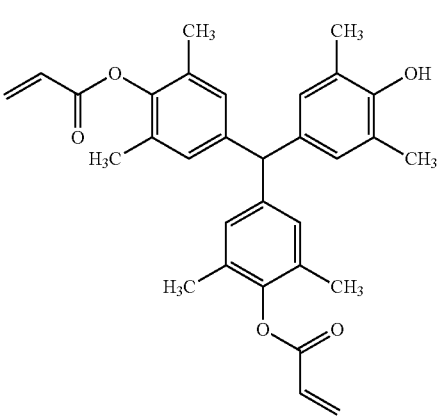

(1-43)
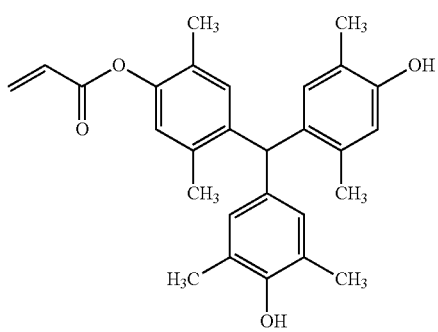
(1-44)
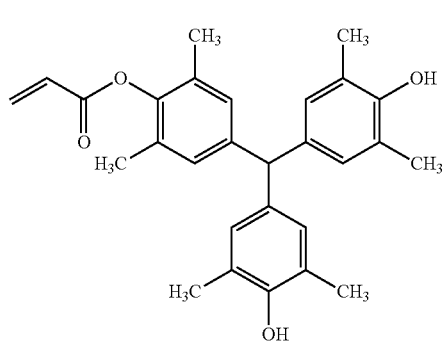
(1-45)
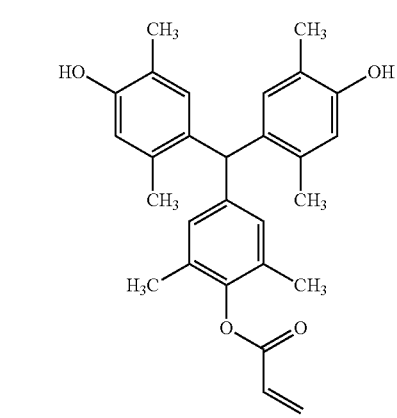
(1-46)
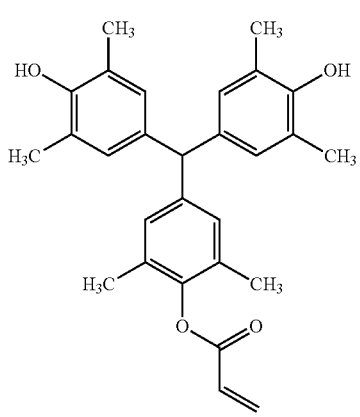
(1-47)
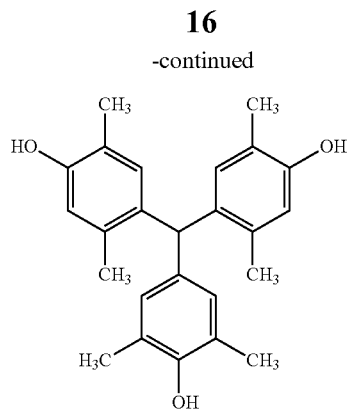
(1-48)
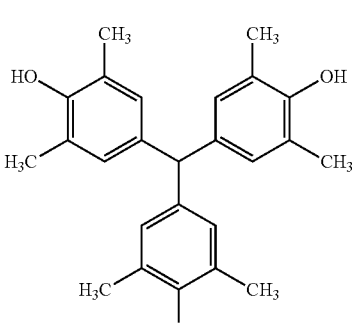
[Chem. 7]
(1-49)
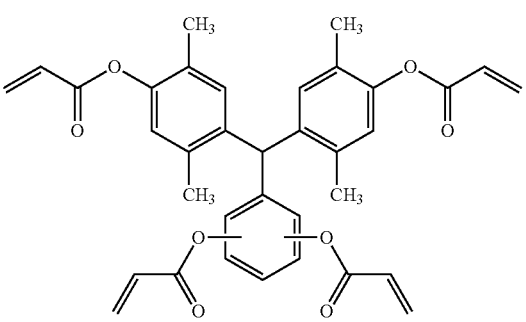
(1-50)
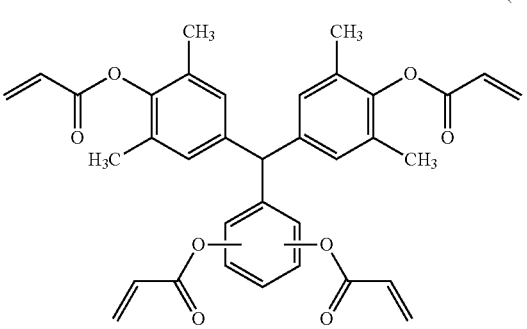

(1-51)
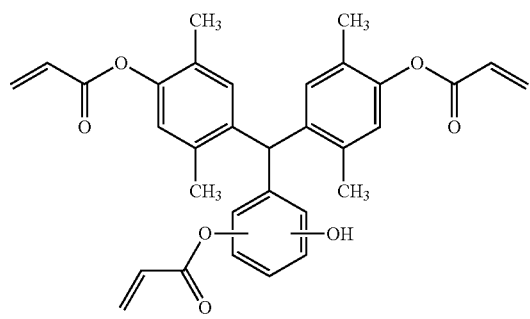
(1-52)
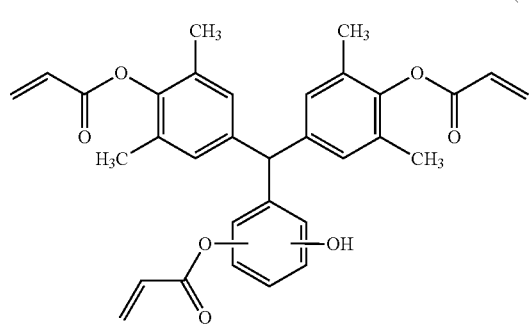
(1-53)
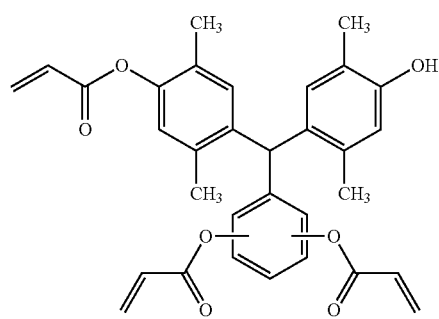
(1-54)
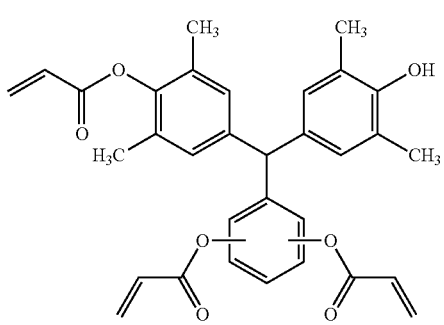
(1-55)
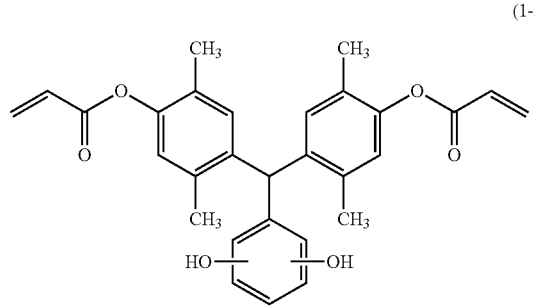
(1-56)
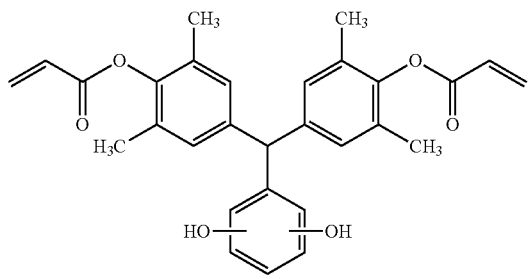
(1-57)
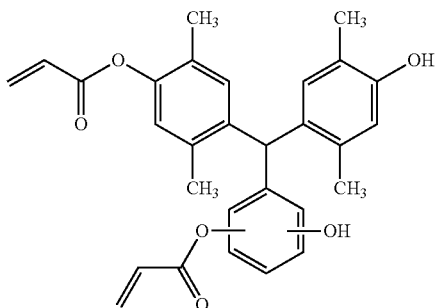
(1-58)
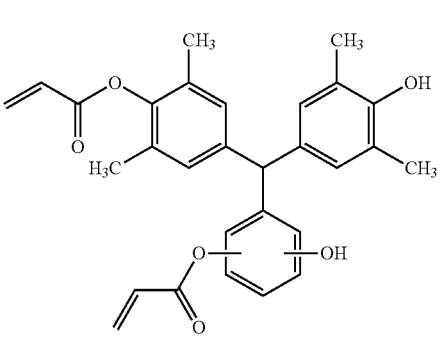
[Chem. 8]
(1-59)
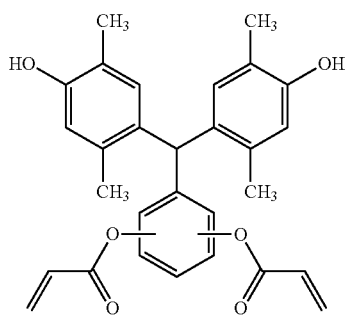
(1-60)
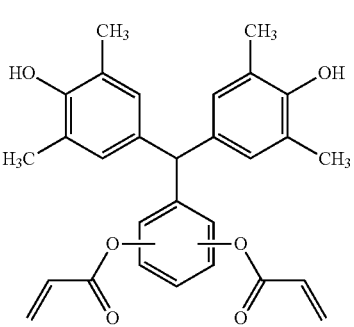

(1-61)
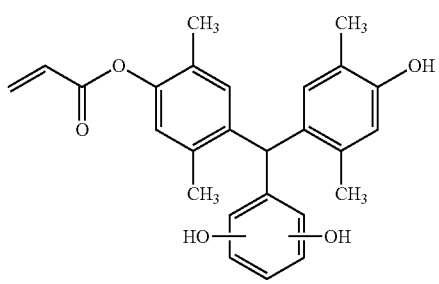

(1-62)
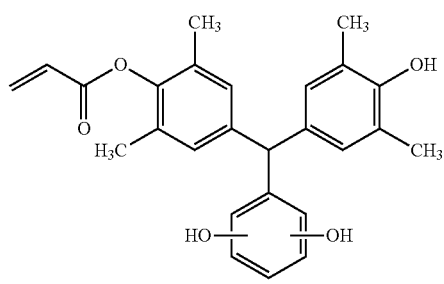

(1-63)
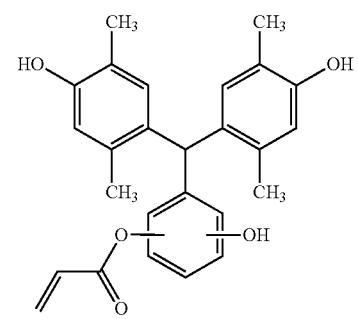

(1-64)
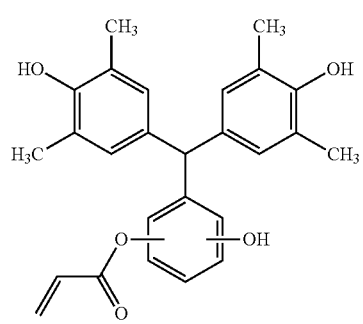

(1-65)
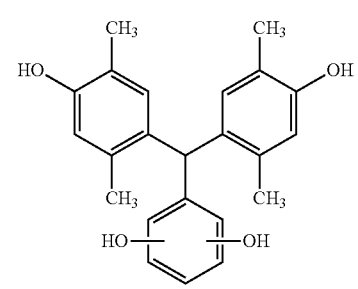

(1-66)
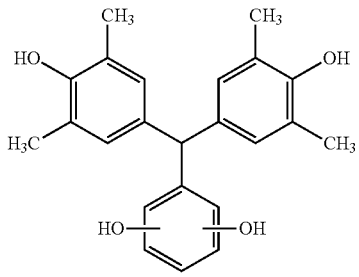

In the phenolic hydroxyl group-containing compound of the present invention, in the general formula (1), at least one of V, W, X, and Y is a hydroxyl group, and at least one of V, W, X, and Y is a (meth)acryloyloxy group. Among these, V in the general formula (1) is preferably a hydrogen atom from the viewpoint of industrial easy availability of raw materials and the ease of reaction design.

Also, the bond position of each of W, X, and Y in the general formula (1) is preferably the para-position with respect to a methine group bridging the three aromatic rings because a cured product having high heat resistance can be produced. Therefore, the phenolic hydroxyl group-containing compound of the present invention more preferably has a molecular structure represented by general formula (2) below,

[Chem. 9]

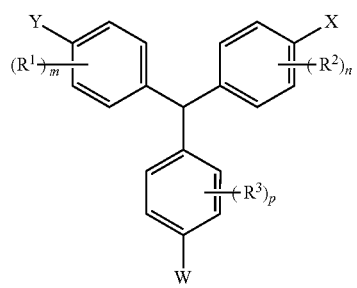

(2)

[in the formula, $R^1$, $R^2$, and $R^3$ are each independently an alkyl group having 1 to 8 carbon atoms, m and n are each independently an integer of 1 to 4, p is an integer of 0 to 4, and W, X, and Y are each independently a (meth)acryloyloxy group or a hydroxyl group], wherein at least one of W, X, and Y is a hydroxyl group, and at least one of W, X, and Y is a (meth)acryloyloxy group.

Further, in view of higher industrial utility value of the phenolic hydroxyl group-containing compound, preferably, any one of W, X, and Y is a (meth)acryloyloxy group, and the other two are hydroxyl groups.

The industrial utility value of the phenolic hydroxyl group-containing compound, that is, the utility methods thereof include various methods such as the direct use of the phenolic hydroxyl group-containing compound as a curable compound for a radically polymerizable composition, the use in combination with a phenol resin curing agent for a dual curing-type composition, the use for a (meth)acryloyl group-containing resin by reaction with an aldehyde compound as described below, and the like.

The phenolic hydroxyl group-containing compound of the present invention represented by the general formula (1)

may be used as a composition of a plurality of different phenolic hydroxyl group-containing compounds. In this case, the average number of (meth)acryloyloxy groups per molecule of the phenolic hydroxyl group-containing compounds in the composition is preferably in a range of 0.5 to 2.5. The term "average number of (meth)acryloyloxy groups per molecule" represents a value obtained by averaging the numbers of (meth)acryloyloxy groups possessed by the phenolic hydroxyl group-containing compounds in the composition to get a number per molecule. That is, a (meth) acryloyl group-containing resin of the present invention described below may be produced by using singly the phenolic hydroxyl group-containing compound represented by the general formula (1) or using in combination of a plurality of the phenolic hydroxyl group-containing compounds as long as the average number of (meth)acryloyloxy group per molecule in the phenolic hydroxyl group-containing composition used is within a range of 0.5 to 2.5.

When the average number of (meth)acryloyloxy group per molecule in the phenolic hydroxyl group-containing composition is less than 0.5, the content of (meth)acryloyl groups in the (meth)acryloyl group-containing resin produced by using the composition is decreased, thereby failing to achieve satisfactory heat resistance of a cured product thereof.

On the other hand, when the average number of (meth) acryloyloxy groups per molecule in the phenolic hydroxyl group-containing composition exceeds 2.5, the molecular weight of the (meth)acryloyl group-containing resin is not satisfactorily increased due to less condensation reaction with an aldehyde compound, thereby decreasing the heat resistance of a cured product thereof.

In particular, the average number of (meth)acryloyloxy groups per molecule in the phenolic hydroxyl group-containing composition is preferably in a range of 1 to 2 because the final (meth)acryloyl group-containing resin has excellent heat resistance.

The phenolic hydroxyl group-containing compound or composition used in the present invention can be preferably produced by, for example, any one of methods described below.

Method 1: A method including polycondensing alkyl-substituted phenol (a1) with phenolic hydroxyl group-containing aromatic aldehyde (a2) to produce a compound (α) represented by general formula (3),

[Chem. 10]

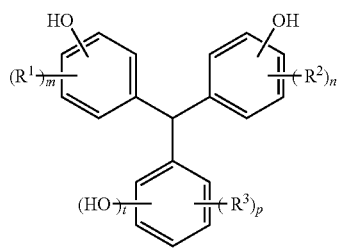

(3)

(in the formula, $R^1$, $R^2$, and $R^3$ are each independently an alkyl group having 1 to 8 carbon atoms, m and n are each independently an integer of 1 to 4, p is an integer of 0 to 4, and t is 1 or 2), and then reacting the compound (α) with a (meth)acrylic acid halide (β).

Method 2: A method including reacting a phenolic hydroxyl group-containing aromatic aldehyde (a2) with a (meth)acrylic acid halide (β) to produce a reaction product (γ) represented by general formula (4) below,

[Chem. 11]

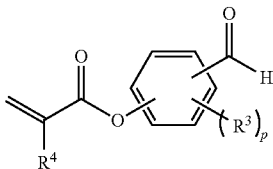

(4)

(in the formula, $R^3$ is an alkyl group having 1 to 8 carbon atoms, p is an integer of 0 to 4, and $R^4$ is a hydrogen atom or a methyl group), and then reacting the reaction product (γ) with the alkyl-substituted phenol (a1).

In the present invention, "(meth)acrylic acid" represents one or both of "acrylic acid" and "methacrylic acid".

The alkyl-substituted phenol (a1) is a compound in which the hydrogen atoms bonded to an aromatic ring of phenol are partially or entirely substituted by alkyl groups, and one compound or combination of two or more compounds may be used. The alkyl group is, for example, an alkyl group having 1 to 8 carbon atoms, and specific examples thereof include a methyl group, an ethyl group, a propyl group, an isopropyl group, a n-butyl group, a tert-butyl group, a pentyl group, a hexyl group, a heptyl group, an octyl group, and the like. In particular, methyl group-substituted phenol is preferred because a cured product has high heat resistance, and specific examples thereof include o-cresol, m-cresol, p-cresol, 2,5-xylenol, 3,5-xylenol, 3,4-xylenol, 2,4-xylenol, 2,6-xylenol, 2,3,5-trimethylphenol, 2,3,6-trimethylphenol, and the like. Among these, 2,5-xylenol and 2,6-xylenol are particularly preferred.

Examples of the phenolic hydroxyl group-containing aromatic aldehyde (a2) include hydroxybenzaldehydes such as 2-hydroxybenzaldehyde, 3-hydroxybenzaldehyde, 4-hydroxybenzaldehyde, and the like; dihydroxybenzaldehyde such as 2,4-dihydroxybenzaldehyde, 3,4-dihydroxybenzaldehyde, and the like; alkyl group-containing hydroxybenzaldehydes such as 2-hydroxy-4-methylbenzaldehyde, 2-hydroxy-5-methylbenzaldehyde, 2-hydroxy-3,5-dimethylbenzaldehyde, 4-hydroxy-3,5-dimethylbenzaldehyde, and the like. These may be used alone or in combination of two or more. In particular, in view of industrial easy availability and excellent balance between heat resistance and alkali solubility, hydroxybenzaldehydes are preferred, and 4-hydroxybenzaldehyde and 4-hydroxy-3,5-dimethylbenzaldehyde are more preferred.

Examples of a halide as the (meth)acrylic acid halide (β) include fluorine, chlorine, bromine, iodine, and astatine, and examples of the (meth)acrylic acid halide include (meth) acrylic chloride, (meth)acrylic bromide, (meth)acrylic iodide, and the like. Among these, (meth)acrylic acid chloride is preferred in view of high reactivity and easy availability.

The method 1 includes, for example, three steps below.
(Step 1-1)
The alkyl-substituted phenol (a1) is polycondensed with the phenolic hydroxyl group-containing aromatic aldehyde (a2) in the presence of an acid catalyst to produce a crude product containing the compound (α) represented by the general formula (3) in a reaction solution.

(Step 1-2)

The compound (α) produced in the step 1-1 is recovered (isolated) from the reaction solution.

(Step 1-3)

The compound (α) isolated in the step 1-2 is reacted with the (meth)acrylic acid halide (β) in the presence of a base.

Examples of the acid catalyst used in the step 1-1 include acetic acid, oxalic acid, sulfuric acid, hydrochloric acid, phenolsulfonic acid, para-toluenesulfonic acid, zinc acetate, manganese acetate, and the like. These acid catalysts may be used alone or in combination of two or more. Among these, in view of excellent catalytic activity, para-toluenesulfonic acid is preferred. The acid catalyst may be added before or during the reaction of the alkyl-substituted phenol (a1) with the phenolic hydroxyl group-containing aromatic aldehyde (a2).

If required, the step 1-1 may be performed in the presence of an organic solvent. Examples of the organic solvent used include monoalcohols such as methanol, ethanol, propanol, and the like; polyols such as ethylene glycol, 1,2-propanediol, 1,3-propanediol, 1,4-butanediol, 1,5-pentanediol, 1,6-hexanediol, 1,7-heptanediol, 1,8-octanediol, 1.9-nonanediol, trimethylene glycol, diethylene glycol, polyethylene glycol, glycerin, and the like; glycol ethers such as 2-ethoxyethanol, ethylene glycol monomethyl ether, ethylene glycol monoethyl ether, ethylene glycol monopropyl ether, ethylene glycol monobutyl ether, ethylene glycol monopentyl ether, ethylene glycol dimethyl ether, ethylene glycol ethyl methyl ether, ethylene glycol monophenyl ether, and the like; cyclic ethers such as 1,3-dioxane, 1,4-dioxane, tetrahydrofuran, and the like; glycol esters such as ethylene glycol acetate and the like; ketones such as acetone, methyl ethyl ketone, methyl isobutyl ketone, and the like. These solvents can be used alone or in combination of two or more. Among these, 2-ethoxyethanol is preferred from the viewpoint of excellent solubility of the resultant compound.

The temperature of reaction of the alkyl-substituted phenol (a1) with the phenolic hydroxyl group-containing aromatic aldehyde (a2) in the step 1-1 is, for example, 60° C. to 140° C. In addition, the reaction time is, for example, 0.5 to 100 hours.

The ratio [(a1)/(a2)] of the alkyl-substituted phenol (a1) to the phenolic hydroxyl group-containing aromatic aldehyde (a2) charged in the step 1-1 is preferably within a range of 1/0.2 to 1/0.5 and more preferably within a range of 1/0.25 to 1/0.45 in terms of molar ratio because unreacted alkyl-substituted phenol can be easily removed, the yield of the product is high, and the compound (α) can be produced with high purity.

Examples of the compound (α) produced in the step 1-1 include compounds represented by general formulae (3-1) to (3-10) below.

[Chem. 12]

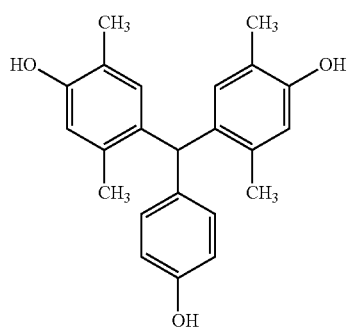

(3-1)

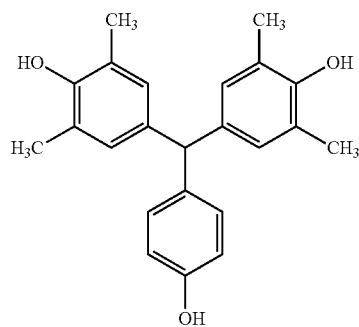

(3-2)

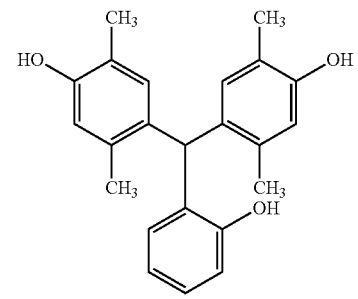

(3-3)

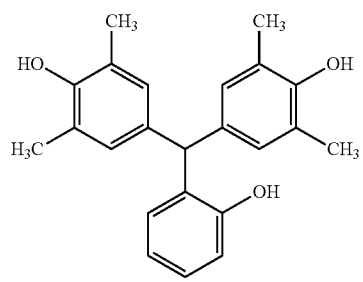

(3-4)

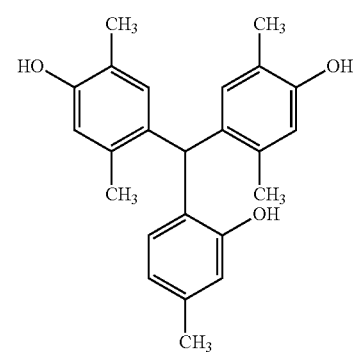

(3-5)

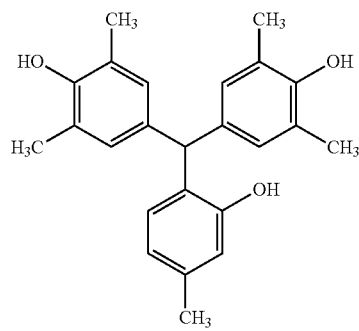

(3-6)

(3-7)
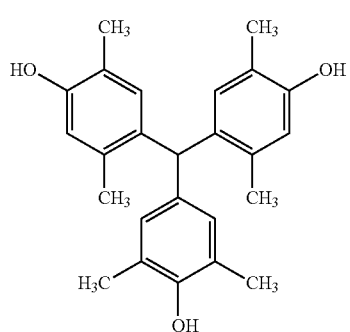

(3-8)
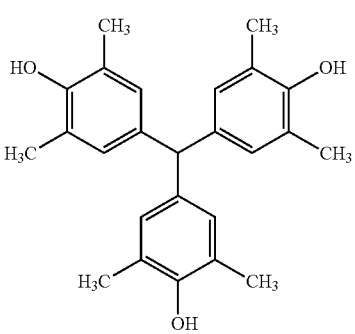

(3-9)
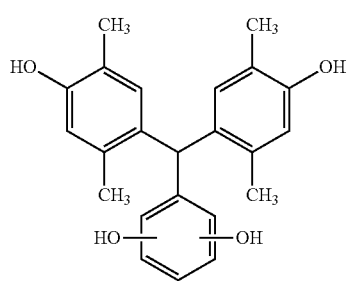

(3-10)
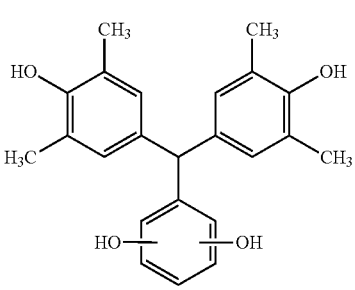

The reaction solution produced in the step 1-1 may contain, together with the compound (α), the uncreated alkyl-substituted phenol (a1) and aromatic aldehyde (a2) remaining therein. Also, the reaction solution may contain a component having a molecular structure other than the structure represented by the general formula (3). Therefore, the purity of the compound (α) is preferably increased as much as possible by an isolation operation as in the step 1-2.

The purity of the compound (α) to be reacted with the (meth)acryloyl acid halide (β) is preferably 85% or more, more preferably 90% or more, still more preferably 94% or more, particularly preferably 98% or more, and most preferably 100%. The purity of the compound (α) can be determined from an area ratio in a chart of gel permeation chromatography (GPC).

In the present invention, GPC measurement conditions are as follows.

[GPC Measurement Conditions]

Measuring apparatus: "HLC-8220 GPC" manufactured by Tosoh Corporation

Column: "Shodex KF802" (8.0 mmϕ×300 mm) manufactured by Showa Denko K. K.

+"Shodex KF802" (8.0 mmϕ×300 mm) manufactured by Showa Denko K. K.

+"Shodex KF803" (8.0 mmϕ×300 mm) manufactured by Showa Denko K. K.

+"Shodex KF804" (8.0 mmϕ×300 mm) manufactured by Showa Denko K. K.

Column temperature: 40° C.

Detector: RI (differential refractometer)

Data processing: "GPC-8020 model II version 4.30" manufactured by Tosoh Corporation Developing solvent: tetrahydrofuran Flow rate: 1.0 ml/min Sample: prepared by filtering a 0.5 mass % tetrahydrofuran solution in terms of resin solid with a microfilter.

Injection amount: 0.1 ml

Standard sample: monodisperse polystyrene described below.

(Standard Sample: Monodisperse Polystyrene)

"A-500" manufactured by Tosoh Corporation

"A-2500" manufactured by Tosoh Corporation

"A-5000" manufactured by Tosoh Corporation

"F-1" manufactured by Tosoh Corporation

"F-2" manufactured by Tosoh Corporation

"F-4" manufactured by Tosoh Corporation

"F-10" manufactured by Tosoh Corporation

"F-20" manufactured by Tosoh Corporation

In the step 1-2, impurities such as the uncreated alkyl-substituted phenol (a1) and aromatic aldehyde (a2), etc. are removed from the compound (α), and thus the resultant phenolic hydroxyl group-containing composition has high crystallinity. As a result, a cured product of the (meth)acryloyl group-containing resin produced by using the composition has a glass transition temperature of 400° C. or more and thus has heat resistance of two times or more as high as usual cured products.

The step 1-2 is a step of isolating the compound (α), by, for example, a method including pouring the reaction solution after the completion of the step 1-1 into a poor solvent (S1) in which the compound (α) is insoluble or slightly soluble and filtering off the produced precipitate. Next, the produced precipitate is redissolved in a solvent (S2) which highly dissolves the compound (α) and is miscible with the poor solvent (S1). Further, the resultant solution is poured into the poor solvent (S1), and the compound (α) with high purity is filtered off as a precipitate. Examples of the poor solvent (S1) used include water, monoalcohols such as methanol, ethanol, propanol, ethoxyethanol, and the like; aliphatic hydrocarbons such as n-hexane, n-heptane, n-octane, cyclohexane, and the like; and aromatic hydrocarbons such as toluene, xylene, and the like. Among these poor solvents (S1), water, methanol, and ethoxyethanol are preferred because the acid catalyst used in the step 1-1 has high solubility and the acid catalyst can be efficiently removed at the same time as isolation of the compound (α).

On the other hand, examples of the solvent (S2) include monoalcohols such as methanol, ethanol, propanol, and the like; polyols such as ethylene glycol, 1,2-propanediol, 1,3-propanediol, 1,4-butanediol, 1,5-pentanediol, 1,6-hexanediol, 1,7-heptanediol, 1,8-octanediol, 1.9-nonanediol, trimethylene glycol, diethylene glycol, polyethylene glycol, glycerin, and the like; glycol ethers such as 2-ethoxyethanol, ethylene glycol monomethyl ether, ethylene glycol monoethyl ether, ethylene glycol monopropyl ether, ethylene glycol monobutyl ether, ethylene glycol monopentyl ether, ethylene glycol dimethyl ether, ethylene glycol ethyl methyl ether, ethylene glycol monophenyl ether, and the like; cyclic ethers such as 1,3-dioxane, 1,4-dioxane, and the like; glycol esters such as ethylene glycol acetate and the like; ketones such as acetone, methyl ethyl ketone, methyl isobutyl ketone, and the like. When water or monoalcohol is used as the poor solvent (S1), the (S2) is preferably acetone. The poor solvents (S1) can be used alone or in combination of two or more and also the solvents (S2) can be used alone or in combination of two or more.

Examples of the base used in the step 1-3 include alkali metal hydroxides such as sodium hydroxide, potassium hydroxide, and the like; alkali metal carbonates such as sodium carbonate, potassium carbonate, cesium carbonate, and the like; tertiary amines such as triethylamine, trimethylamine, and the like; pyridine; and the like. Among these bases, potassium carbonate and tertiary amines are preferred, and potassium carbonate and trimethylamine are particularly preferred because the base can be easily removed from the reaction system after the reaction of the compound (α) with the (meth)acrylic acid halide (β).

If required, a solvent may be used in the step 1-3. Examples of the solvent include monoalcohols such as methanol, ethanol, propanol, and the like; polyols such as ethylene glycol, 1,2-propanediol, 1,3-propanediol, 1,4-butanediol, 1,5-pentanediol, 1,6-hexanediol, 1,7-heptanediol, 1,8-octanediol, 1,9-nonanediol, trimethylene glycol, diethylene glycol, polyethylene glycol, glycerin, and the like; glycol ethers such as 2-ethoxyethanol, ethylene glycol monomethyl ether, ethylene glycol monoethyl ether, ethylene glycol monopropyl ether, ethylene glycol monobutyl ether, ethylene glycol monopentyl ether, ethylene glycol dimethyl ether, ethylene glycol ethyl methyl ether, ethylene glycol monophenyl ether, and the like; cyclic ethers such as 1,3-dioxane, 1,4-dioxane, tetrahydrofuran, and the like; glycol esters such as ethylene glycol acetate and the like; ketones such as acetone, methyl ethyl ketone, methyl isobutyl ketone, and the like. These solvents can be used alone or in combination of two or more. Among these, tetrahydrofuran, methyl ethyl ketone, and methyl isobutyl ketone are preferred from the viewpoint of excellent solubility of the resultant compound.

The temperature of reaction of the compound (α) with the (meth)acrylic acid halide (β) in the step 1-3 is, for example, 20° C. to 80° C. In addition, the reaction time is, for example, 1 to 30 hours.

The ratio of the compound (α) to the (meth)acrylic acid halide (β) charged in the step 1-3 is preferably within a range of 1/0.5 to 1/3 and more preferably within a range of 1/1 to 1/2 in terms of molar ratio [(α')/(β)] wherein α' is the number of moles of phenolic hydroxyl groups possessed by the compound (α) because the average number of (meth)acryloyloxy groups per molecule of the compound (α) in the intended phenolic hydroxyl group-containing composition can be easily controlled to a range of 0.5 to 2.5.

The method 2 for producing the phenolic hydroxyl group-containing composition used in the present invention includes, for example, three steps below.

(Step 2-1)

The phenolic hydroxyl group-containing aromatic aldehyde (a2) is reacted with the (meth)acrylic acid halide (β) in the presence of a base to produce a crude product containing the reaction product (γ) represented by the general formula (4).

(Step 2-2)

The reaction product (γ) produced in the step 2-1 is recovered (isolated) from the reaction solution.

(Step 2-3)

The reaction product (γ) isolated in the step 2-2 is reacted with alkyl-substituted phenol (a1) in the presence of an acid catalyst.

The examples of the compound used in the step 1-3 of the method 1 can be used as the base used in the step 2-1. The bases can be used alone or in combination of two or more. Among the bases, in view of the ease of removal from the reaction system after the reaction between the aromatic aldehyde (a2) and the (meth)acrylic acid halide (β), potassium carbonate and tertiary amines are preferred, and potassium carbonate and triethylamine are more preferred.

If required, the step 2-1 may be performed in the presence of an organic solvent. For example, the solvent used in the step 1-1 of the method 1 can be used as the organic solvent. These solvents can be used alone or in combination of two or more. Among these, tetrahydrofuran, methyl ethyl ketone, and methyl isobutyl ketone are preferred from the viewpoint of excellent solubility of the resultant compound.

The temperature of reaction of the aromatic aldehyde (a2) with the (meth)acrylic acid halide (β) in the step 2-1 is, for example, 20° C. to 100° C. In addition, the reaction time is, for example, 1 to 30 hours.

The ratio [(a2)/(β)] of the aromatic aldehyde (a2) to the (meth)acrylic acid halide (β) charged in the step 2-1 is preferably within a range of 1/1 to 1/5 and more preferably within a range of 1/1 to 1/3 in terms of ratio of the number of moles of hydroxyl groups possessed by the aromatic aldehyde (a2) to the number of moles of halogen atoms possessed by the (meth)acrylic acid halide (β) because the reaction product (γ) can be obtained in high yield.

Examples of the reaction product (γ) produced in the step 2-1 include compounds represented by general formulae (4-1) to (4-4) below.

[Chem. 13]

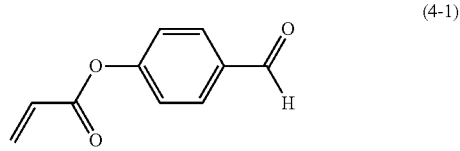

(4-1)

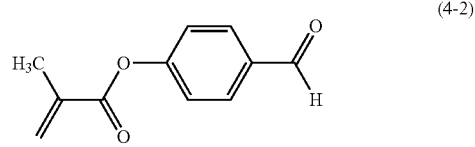

(4-2)

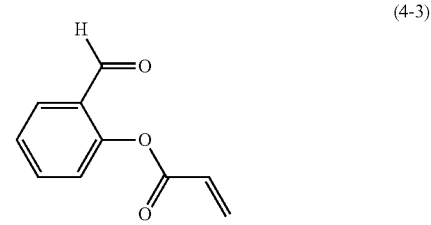

(4-3)

(4-4)

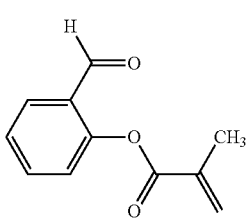

The reaction solution produced in the step 2-1 may contain, together with the reaction product (γ), the uncreated aromatic aldehyde (a2) and (meth)acrylic acid halide (β) remaining therein. Also, the reaction solution may contain a component having a molecular structure other than the structure represented by the general formula (4). Therefore, the purity of the reaction product (γ) is preferably increased as much as possible by an isolation operation as in the step 2-1.

The purity of the reaction product (γ) to be reacted with the alkyl-substituted phenol (a1) is preferably 85% or more, more preferably 90% or more, still more preferably 94% or more, particularly preferably 98% or more, and most preferably 100%. The purity of the reaction product (γ) can be determined from an area ratio in a chart of GPC performed under the conditions described above.

In the step 2-2, impurities such as the uncreated aromatic aldehyde (a2) and (meth)acrylic acid halide (β), etc. are removed from the reaction product (γ), and thus the resultant phenolic hydroxyl group-containing composition has high crystallinity. As a result, a cured product of the (meth)acryloyl group-containing resin produced by using the composition has a glass transition temperature of 400° C. or more and thus has heat resistance of two times or more as high as usual cured products.

The purity of the reaction product (γ) in the step 2-2 by, for example, a method including recovering, by filtration, the crude product containing the reaction product (γ) and present as a solid in the reaction solution, adding the recovered product to a solvent which dissolves the reaction product (γ) to dissolve the reaction product (γ), further adding water to separate between an organic layer in which the reaction product (γ) is dissolved and an aqueous layer, and recovering the reaction product (γ) from the organic layer. Examples of the solvent used to dissolve the reaction product (γ) include chloroform, toluene, xylene, hexane, and the like. In particular, chloroform is preferred because the target reaction product (γ) can be obtained in high yield.

In the step 2-3, the reaction product (γ) produced in the step 2-2 is reacted with the alkyl-substituted phenol (a1) in the presence of an acid catalyst. Examples of the alkyl-substituted phenol (a1) and the acid catalyst include the various compounds exemplified in the method 1. Also, if required, the step 2-3 may be performed in the presence of an organic solvent. For example, the solvent used in the method 1-1 of the method 1 can be used as the organic solvent.

The temperature of reaction of the reaction product (γ) with the alkyl-substituted phenol (a1) in the step 2-3 is, for example, 20° C. to 80° C. In addition, the reaction time is, for example, 1 to 30 hours.

The ratio of the reaction product (γ) to the alkyl-substituted phenol (a1) charged in the step 2-1 is preferably within a range of 1/2 to 1/5 and more preferably within a range of 1/2 to 1/4 in terms of molar ratio [(γ')/(a1)] wherein γ' is the number of moles of aldehyde groups possessed by the reaction product (γ) because the average number of (meth)acryloyloxy groups per molecule in the intended phenolic hydroxyl group-containing composition can be easily controlled to a range of 0.5 to 2.5.

The (meth)acryloyl group-containing resin of the present invention is produced by reacting the phenolic hydroxyl group-containing compound or composition with an aldehyde compound.

Examples of the aldehyde compound used include aromatic aldehyde, aliphatic aldehyde, and the like. Examples of the aromatic aldehyde include benzaldehyde, o-tolualdehyde, salicylaldehyde, cinnamaldehyde, α-naphthaldehyde, and the like. Examples of the aliphatic aldehyde include formaldehyde, para-formaldehyde, acetaldehyde, propionaldehyde, butylaldehyde, isobutylaldehyde, valeraldehyde, isovaleraldehyde, pivalaldehyde, capronaldehyde, heptaldehyde, caprylaldehyde, pelargonaldehyde, caprinaldehyde, undecylaldehyde, laurinaldehyde, tridecylaldehyde, stearinaldehyde, glyoxal, succindialdehyde, glutaraldehyde, and the like. These may be used alone or in combination of two or more. In particular, in view of good reactivity to the phenolic hydroxyl group-containing composition and the ease of production of the (meth)acryloyl group-containing resin of the present invention, the aliphatic aldehyde is preferred and formaldehyde is more preferred.

The reaction of the phenolic hydroxyl group-containing compound or composition with the aldehyde compound can be performed by, for example, a method of reaction at 60° C. to 100° C. for 2 to 20 hours in the presence of an acid catalyst. Examples of the acid catalyst include inorganic acids such as hydrochloric acid, sulfuric acid, phosphoric acid, and the like; organic acids such as methanesulfonic acid, p-toluenesulfonic acid, oxalic acid, and the like; and Lewis acids such as boron trifluoride, anhydrous aluminum chloride, zinc chloride, and the like. The amount of use is preferably in a range of 0.1 to 5% by weight relative to the total weight of the raw materials charged.

The weight-average molecular weight (Mw) of the resultant (meth)acryloyl group-containing resin is preferably 2,000 to 60,000 and more preferably 5,000 to 20,000 because radical polymerization reaction well proceeds.

A curable composition of the present invention contains the phenolic hydroxyl group-containing compound or the (meth)acryloyl group-containing resin as an essential component, and the component may be use singly or may contain another (meth)acryloyl group-containing compound.

Examples of another radically curable compound used include various epoxy (meth)acrylates, other (meth)acrylate compounds, and the like.

Examples of the epoxy(meth)acrylates include various those produced by addition reaction of various polyglycidyl ether compounds with (meth)acrylic acid or halide thereof. Examples of the polyglycidyl ether include polyglycidyl ethers of aromatic polyols such as hydroquinone, 2-methylhydroquinone, 1,4-benzenedimethanol, 3,3'-biphenol, 4,4'-biphenol, tetramethylbiphenol, biphenyl-3,3'-dimethanol, biphenyl-4,4'-dimethanol, bisphenol A, bisphenol B, bisphenol F, bisphenol S, 1,4-naphthalenediol, 1,5-naphthalenediol, 1,6-naphthalenediol, 2,6-naphthalenediol, 2,7-naphthalenediol, naphthalene-2,6-dimethanol, 4,4',4"-methylidine trisphenol, and the like;

polyglycidyl ethers of polyether-modified aromatic polyols produced by ring-opening polymerization of the aromatic polyols with various cyclic ether compounds such as ethylene oxide, propylene oxide, tetrahydrofuran, ethyl glycidyl ether, propylene glycidyl ether, butyl glycidyl ether, phenyl glycidyl ether, allyl glycidyl ether, and the like;

polyglycidyl ethers of lactone-modified aromatic polyols produced by polycondensation of the aromatic polyols with lactone compounds such as ε-caprolactone and the like;

polyglycidyl ethers of aromatic ring-containing polyester polyols produced by reaction of the aromatic polyols with aliphatic dicarboxylic acids such as malonic acid, succinic acid, glutaric acid, adipic acid, pimelic acid, and the like;

polyglycidyl ethers of aromatic ring-containing polyester polyols produced by reaction of aromatic dicarboxylic acids or anhydrides thereof, such as phthalic acid, phthalic anhydride, terephthalic acid, isophthalic acid, orthophthalic acid, and the like, with aliphatic polyols such as ethylene glycol, diethylene glycol, propylene glycol, 1,3-propanediol, 1,4-butanediol, 1,3-butanediol, 3-methyl-1,3-buanediol, 1,5-pentanediol, neopentyl glycol, 1,6-hexanediol, trimethylolethane, trimethylolpropane, glycerin, and the like;

bisphenol-type epoxy resins such as bisphenol A-type epoxy resins, bisphenol B-type epoxy resins, bisphenol F-type epoxy resins, bisphenol S-type epoxy resins, and the like; and novolac-type epoxy resins such as phenolnovolac-type epoxy resins, cresol novolac-type epoxy resins, and the like. These may be used alone or in combination of two or more.

Examples of the other (meth)acrylate compounds include monofunctional (meth)acrylate compounds such as n-butyl (meth)acrylate, isobutyl (meth)acrylate, tert-butyl (meth)acrylate, n-pentyl (meth)acrylate, n-hexyl (meth)acrylate, n-octyl (meth)acrylate, isooctyl (meth)acrylate, 2-ethylhexyl (meth)acrylate, benzyl (meth) acrylate, phenoxyethyl (meth) acrylate, phenoxydiethylene glycol (meth)acrylate, glycidyl (meth)acrylate, morpholine (meth)acrylate, 2-hydroxyethyl (meth)acrylate, 2-hydroxypropyl (meth)acrylate, 4-hydroxybutyl (meth)acrylate, diethylene glycol mono (meth)acrylate, triethylene glycol mono(meth)acrylate, dipropylene glycol mono(meth)acrylate, 2-methoxyethyl (meth) acrylate, methoxydiethylene glycol (meth) acrylate, methoxytriethylene glycol (meth) acrylate, methoxypolyethylene glycol (meth) acrylate, 2-butoxyethyl (meth)acrylate, butoxytriethylene glycol (meth)acrylate, 2-ethoxyethyl (meth)acrylate, 2-(2-ethoxyethoxyl)ethyl (meth)acrylate, ethoxypolyethylene glycol (meth)acrylate, 4-nonylphenoxyethylene glycol (meth) acrylate, tetrahydrofurfuryl (meth)acrylate, caprolactone-modified tetrahydrofurfuryl (meth) acrylate, cyclohexyl (meth) acrylate, isobornyl (meth) acrylate, 2-hydroxy-3-phenoxypropyl (meth) acrylate, cyclohexyl (meth) acrylate, cyclohexylmethyl (meth) acrylate, cyclohexylethyl (meth) acrylate, dicyclopentanyl (meth) acrylate, dicyclopentanyloxethyl (meth) acrylate, dicyclopentenyl (meth) acrylate, dicyclopentenyloxyethyl (meth) acrylate, phenylbenzyl (meth)acrylate, phenylphenoxyethyl acrylate, and the like;

di(meth)acrylate compounds such as ethylene glycol di(meth)acrylate, diethylene glycol di(meth)acrylate, triethylene glycol di(meth)acrylate, polyethylene glycol di(meth)acrylate, propylene glycol di(meth)acrylate, dipropylene glycol di(meth)acrylate, tripropylene glycol di(meth)acrylate, butylene glycol di(meth)acrylate, tetrabutylene glycol di(meth)acrylate, 1,4-butanediol di(meth)acrylate, 1,6-hexanediol di(meth)acrylate, 1,9-nonanediol di(meth)acrylate, neopentyl glycol di(meth)acrylate, di(meth)acrylate of bisphenol A ethylene oxide adduct, di(meth)acrylate of bisphenol A propylene oxide adduct, di(meth)acrylate of bisphenol F ethylene oxide adduct, di(meth)acrylate of bisphenol F propylene oxide adduct, dicyclopentanyl di(meth) acrylate, glycerol di(meth)acrylate, neopentyl glycol hydroxypivalinic acid ester di(meth)acrylate, caprolactone-modified hydroxypivalinic acid neopentyl glycol di(meth) acrylate, tetrabromobisphenol A di(meth)acrylate, hydropivalaldehyde-modified trimethylolpropane di(meth) acrylate, 1,4-cyclohexanedimethanol di(meth)acrylate, bis[(meth)acryloylmethyl]biphenyl, and the like; and tri- or higher-functional (meth)acrylate compounds such as trimethylolpropane tri(meth)acrylate, trimethylolpropane ethylene oxide adduct tri(meth)acrylate, trimethylolpropane propylene oxide adduct tri(meth)acrylate, pentaerythritol tri(meth)acrylate, glycerol tri(meth)acrylate, alkyl-modified dipentaerythritol tri(meth)acrylate, ditrimethylolpropane tetra(meth)acrylate, ditrimethylolpropane ethylene oxide adduct tetra(meth)acrylate, ditrimethylolpropane propylene oxide adduct tetra(meth)acrylate, dipentaerythritol penta(meth)acrylate, dipentaerythritol hexa(meth)acrylate, and the like. These may be used alone or in combination of two or more.

The content of the other (meth)acryloyl group-containing compound in the curable composition may be within a range where the effect of the present invention of exhibiting excellent heat resistance of a cured product is not impaired. Specifically, the content of the phenolic hydroxyl group-containing compound or (meth)acryloyl group-containing resin of the present invention is preferably 50 parts by mass or more and more preferably 80 parts by mass or more in a total of 100 parts by mass of the phenolic hydroxyl group-containing compound or (meth)acryloyl group-containing resin of the present invention and the other (meth)acryloyl group-containing compound.

The curable composition of the present invention can be formed into a cured product by further adding a photopolymerization initiator, such as an intermolecular cleavage-type photopolymerization initiator or hydrogen abstraction-type photopolymerization initiator, and curing the composition by applying active energy rays or heat.

Examples of the intermolecular cleavage-type photopolymerization initiator include acetophenone compounds such as 1-hyroxycyclohexyl phenyl ketone, diethoxyacetophenone, 2-hydroxy-2-methyl-1-phenylpropan-1-one, benzyldimethyl ketal, 1-(4-isopropylphenyl)-2-hydroxy-2-methylpropan-1-one, 4-(2-hydroxyethoxyl)phenyl-(2-hydroxy-2-propyl) ketone, 2-methyl-2-morpholino(4-thiomethylphenyl)propan-1-one, 2-benzyl-2-dimethylamino-1-(4-morpholinophenyl)-butanone, and the like; benzoins such as benzoin, benzoin methyl ether, benzoin isopropyl ether, and the like; acylphosphine oxide compounds such as 2,4,6-trimethylbenzoin diphenylphosphine oxide, bis(2,4,6-trimethylbenzoyl)-phenyl phosphine oxide, and the like; azo compounds such as 1,1'-azobisisobutyronitrile, 1,1'-azobiscyclohexane carbonitrile, 2-cycano-2-propylazoformamide, and the like; benzyl; methylphenyl glyoxyester; and the like.

Example of the hydrogen abstraction-type photopolymerization initiator include benzophenone compounds such as benzophenone, o-benzoylbenzoic acid methyl-4-phenylbenzophenone, 4,4'-dichlorbenzophenone, hydroxybenzophenone, 4-benzoyl-4'-methyl-diphenyl sulfide, acrylated benzophenone, 3,3',4,4'-tetra(tert-butylperoxycarbonyl)benzophenone, 3,3'-dimethyl-4-methoxybenzophenone, and the like; thioxanthone compounds such as 2-isopropylthioxanthone, 2,4-dimethylthioxanthone, 2,4-diethylthioxanthone, 2,4-dichlorothioxanthone, and the like; aminobenzophenone compounds such as Michler ketone, 4,4'-diethylaminobenzophenone, and the like; 10-butyl-2-chloroacridone; 2-ethylanthraquinone; 9,10-phenanthrenequinone; camphorquinone; and the like.

Among the photopolymerization initiators, acetophenone compounds such as 1-hyroxycyclohexyl phenyl ketone, 2-hydroxy-2-methyl-1-phenylpropan-1-one, 1-(4-isopropylphenyl)-2-hydroxy-2-methylpropan-1-one, 4-(2-hydroxyethoxyl)phenyl-(2-hydroxy-2-propyl) ketone, 2-methyl-2-morpholino(4-thiomethylphenyl)propan-1-one, 2-benzyl-2-dimethylamino-1-(4-morpholinophenyl)-butanone, and the like; and benzophenone are preferred, and 1-hyroxycyclohexyl phenyl ketone is particularly preferred. Also, these photopolymerization initiators can be used alone or in combination of two or more.

The amount of the photopolymerization initiator used is preferably 0.01 to 20 parts by mass, more preferably 0.1 to 15% by mass, and still more preferably 0.5 to 10 parts by mass relative to 100 parts by mass of the curable composition. When electron beams described below are used as the active energy rays, the photopolymerization initiator is not required.

Examples of the active energy rays used for curing the curable composition include ultraviolet light, and ionizing radiation such as electron beams, α-rays, β-rays, γ-rays, and the like. Examples of an energy source or curing apparatus which generates the active energy rays include a sterilization lamp, an ultraviolet lamp (black light), a carbon arc, a xenon lamp, a high-pressure mercury lamp for copying, a medium or high-pressure mercury lamp, an extra-high-pressure mercury lamp, an electrodeless lamp, a metal halide lamp, a ArF excimer laser, an ultraviolet LED, ultraviolet light from natural light as a light source, electron beams from a scanning-type or curtain-type electron beam accelerator, and the like.

When the curable composition is cured by heat radical polymerization, a heat radical polymerization initiator is used. Examples of the heat radical polymerization initiator include organic peroxides such as benzoyl peroxide, di-tert-butyl peroxide, dicumyl peroxide, 3,3,5-trimethylhexanoyl peroxide, di-2-ethylhexyl peroxydicarbonate, methylethyl ketone peroxide, tert-butyl peroxyphthalate, tert-butyl peroxybenzoate, di-tert-butyl peroxyacetate, tert-butyl peroxyisobutylate, tert-butyl peroxy-2-hexanoate, tert-butyl peroxy-3,3,5-trimethylhexanoate, and the like; and azo compounds such as 1,1'-azobisisobutyronitrile, 1,1'-azobiscyclohexane carbonitrile, 2-cyano-2-propylazoformamide, and the like. Among these heat radical polymerization initiators, benzoyl peroxide and 1,1'-azobisisobutyronitrile are preferred. Also, these heat radical polymerization initiators can be used alone or in combination of two or more.

The amount of the heat radical polymerization initiator used is preferably 0.01 to 20 parts by mass, more preferably 0.1 to 15% by mass, and still more preferably 0.5 to 10 parts by mass relative to 100 parts by mass of the curable composition.

EXAMPLES

The present invention is described in further detail below by giving examples. A method for measuring a NMR spectrum used for identifying a compound is as follows.
[1H-NMR Spectrum Measuring Method]
Structural analysis was performed by using "JNM-GSX500 (500 MHz, DMSO-d6, TMS)" manufactured by JEOL Ltd.

Example 1

Production of Phenolic Hydroxyl Group-Containing Composition (1)

In a 100-ml two-necked flask provided with a cooling tube, 7.32 g (60 mmol) of 2,5-xylenol and 2.44 g (20 mmol) of 4-hydroxybenzaldehyde were charged and dissolved in 20 ml of 2-ethoxyethanol. Then, 2 ml of sulfuric acid was added to the resultant solution under cooling in an ice bath, and reaction was performed by heating under stirring for 2 hours in an oil bath of 100° C. After the reaction, a reprecipitation operation was performed by adding water to the resultant solution, thereby producing a crude product. The crude product was re-dissolved in acetone, further reprecipitation was performed with water, and then the resultant product was filtered off and dried under vacuum to produce 5.93 g of light brown crystals of compound (a1) described below. The purity of the compound (a1) in the crude product was 87% by mass in terms of area ratio in GPC, and the purity of the final resultant compound (a1) was 99% by mass.

[Chem. 14]

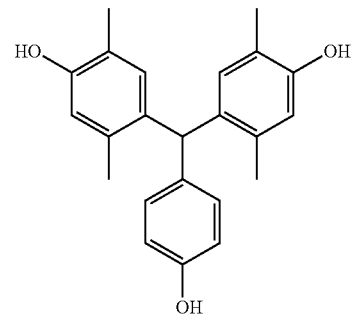

In a 100-ml two-necked flask provided with a cooling tube, 1.74 g (5 mmol) of the compound (α1), 4.10 g (30 mmol) of potassium carbonate, and 10 ml of tetrahydrofuran were charged, and stirring was started. Then, 0.90 g (10 mmol) of acrylic chloride was added dropiwse to the resultant mixture over 30 minutes under cooling in an ice bath, and then reaction was performed by heating under stirring for 12 hours in an oil bath of 70° C. After the reaction, a solid was filtered off from the resultant solution, and a filtrate was mixed with 30 ml of chloroform and washed with 50 ml of water three times. An organic layer which was an under layer was separated and then dehydrated with sodium sulfate, and the solvent was distilled off under reduced pressure to produce 1.79 g of white needle crystals of phenolic hydroxyl group-containing composition (1). As a result of identification from peaks in 1H-NMR, it was confirmed that the target compound having an average number of acryloyloxy groups per molecule of 1.0 is produced. A typical structure of the target compound contained in the phenolic hydroxyl group-containing composition (1) is shown below. Also, FIG. 1 shows a chart of a 1H-NMR spectrum of the phenolic hydroxyl group-containing composition (1).

[Chem. 15]

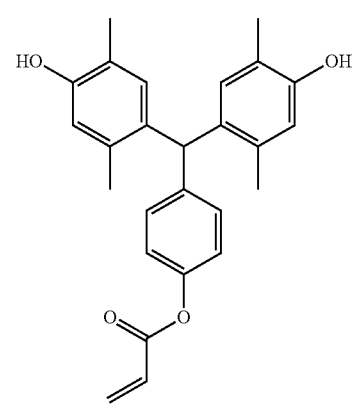

-continued

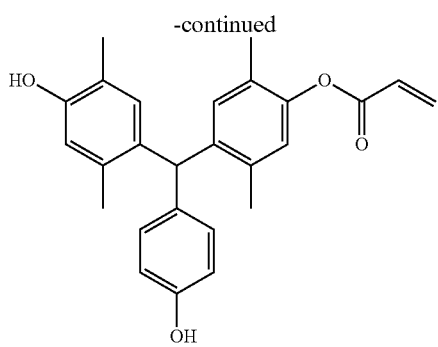

Example 2

Production of Phenolic Hydroxyl Group-Containing Compound (2)

In a 100-ml two-necked flask provided with a cooling tube, 2.44 g (20 mmol) of 4-hydroxybenzaldehyde, 8.20 g (60 mmol) of potassium carbonate, and 40 ml of tetrahydrofuran were charged, and stirring was started. Then, 1.80 g (20 mmol) of acrylic acid chloride was added dropiwse to the resultant mixture over 30 minutes under cooling in an ice bath, and then reaction was performed by heating under stirring for 12 hours in an oil bath of 70° C. After the reaction, a solid was filtered off from the resultant solution, and a filtrate was mixed with 120 ml of chloroform and washed with 200 ml of water three times. An organic layer which was an under layer was separated and then dehydrated with sodium sulfate, and the solvent was distilled off under reduced pressure to produce 2.38 g of white needle crystals of compound (γ1). As a result of identification from peaks in 1H-NMR, it was confirmed that the target compound shown below is produced.

[Chem. 16]

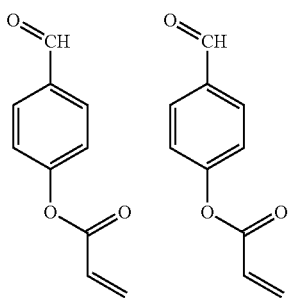

In a 100-ml two-necked flask provided with a cooling tube, 3.66 g (30 mmol) of 2,5-xylenol and 2.07 g (15 mmol) of the compound (γ1) were charged and dissolved in 20 ml of 2-ethoxyethanol. Then, 1 ml of sulfuric acid was added to the resultant solution under cooling in an ice bath, and then reaction was performed by heating under stirring for 2 hours in an oil bath of 100° C. After the reaction, a reprecipitation operation was performed by adding water to the resultant solution, thereby producing a crude product. The crude product was re-dissolved in acetone, further reprecipitation was performed with water, and then the resultant product was filtered off and dried under vacuum to produce 2.42 g of light brown crystals of phenolic hydroxyl group-containing compound (2). As a result of identification from peaks in 1H-NMR, it was confirmed that the target compound having an average number of acryloyloxy groups per molecule of 1.0 is produced. A structure of the phenolic hydroxyl group-containing compound (2) is shown below.

[Chem. 17]

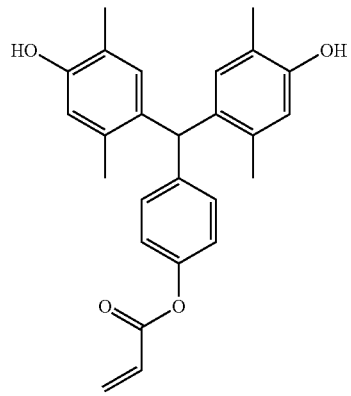

Example 3

Production of (Meth)Acryloyl Group-Containing Resin (1)

In a 100-ml two-necked flask provided with a cooling tube, 0.5 g of the phenolic hydroxyl group-containing composition (1), 0.07 g of para-formaldehyde, and 10 ml of 2-ethoxyethanol were charged, and stirring was started. Then, 0.1 ml of sulfuric acid was added to the resultant mixture under cooling in an ice bath, and then reaction was performed by heating under stirring for 4 hours in an oil bath of 70° C. Next, a reprecipitation operation was performed by adding water to the reaction product, thereby producing a crude product. The crude product was re-dissolved in acetone, further reprecipitation was performed with water, and then the resultant product was filtered off and dried under vacuum to produce 0.4 g of (meth)acryloyl group-containing resin (1).

Example 4

Production of (Meth)Acryloyl Group-Containing Resin (2)

A (meth)acryloyl group-containing resin (2) was produced by the same method as in Example 3 except that the phenolic hydroxyl group-containing compound (2) was used in place of the phenolic hydroxyl group-containing composition (1).

Comparative Production Example 1

Production of (Meth)Acryloyl Group-Containing Resin (1') for Comparison

In a reactor, 150 g of phenol novolac epoxy resin (epoxy equivalent: 190 g/eq), 30 g of acrylic acid, and 80 g of propylene glycol monomethyl acetate as a solvent were charged and reacted at 100° C. for 5 hours to produce 174 g of (meth)acryloyl group-containing resin (1').

Comparative Production Example 2

Production of (Meth)Acryloyl Group-Containing Resin (2') for Comparison

In a reactor, 276 g of cresol novolac resin (epoxy equivalent: 220 g/eq), 67 g of acrylic acid, and 125 g of propylene glycol monomethyl acetate as a solvent were charged and reacted at 100° C. for 6 hours to produce 290 g of (meth) acryloyl group-containing resin (2').

Examples 5 and 6

A cured product was formed according to procedures below and evaluated with respect to heat resistance. The results are shown in Table 1.

In a Schlenk flask, 0.4 g of the (meth)acryloyl group-containing resin (1) or (2) produced in Example 3 or 4, 0.04 g of a polymerization initiator ("Irgacure 184" manufactured by Ciba Specialty Chemicals Inc.,) and 0.5 g of tetrahydrofuran were placed and freeze-dried in a nitrogen atmosphere. The reactor was closed and irradiated with light for 3 hours from a high-pressure mercury lamp provided with a 340 nm band pass filter. Then, the resultant reaction product was added to methanol to be re-precipitated, and the precipitate was filtered off and dried in vacuum to yield a cured product (1) or (2).
Evaluation of Heat Treatment The heat resistance of the resultant cured product (1) or (2) was evaluated by the glass transition temperature. The glass transition temperature was measured by scanning under the conditions of a temperature range of 25° C. to 450° C. and a heating rate of 10° C./min in a nitrogen atmosphere using a differential scanning calorimeter ("DSC Q100" manufactured by TA Instruments Co., Ltd.).

Comparative Examples 1 and 2

A cured product was formed according to procedures below and evaluated with respect to heat resistance. The results are shown in Table 1.

In a Schlenk flask, 0.5 g of the (meth)acryloyl group-containing resin (1') or (2') produced in Comparative Production Example 1 or 2, 0.05 g of a polymerization initiator ("Irgacure 184" manufactured by Ciba Specialty Chemicals Inc.,) and 0.5 g of tetrahydrofuran were placed and freeze-dried in a nitrogen atmosphere. The reactor was closed and irradiated with light for 3 hours from a high-pressure mercury lamp provided with a 340 nm band pass filter. Then, the resultant reaction product was dissolved in methanol and re-precipitated, and the precipitate was filtered off and dried in vacuum to yield a cured product (1') or (2').
Evaluation of Heat Treatment The heat resistance of the resultant cured product (1') or (2') was evaluated by the same method as in Examples 5 and 6.

TABLE 1

| | Example 5 | Example 6 | Comparative Example 1 | Comparative Example 2 |
|---|---|---|---|---|
| Glass transition temperature (° C.) | >400 | >400 | 160 | 160 |

The invention claimed is:

1. A phenolic hydroxyl group-containing composition comprising a plurality of phenolic hydroxyl group-containing compounds represented by the general formula (1) below,

[Chem. 1]

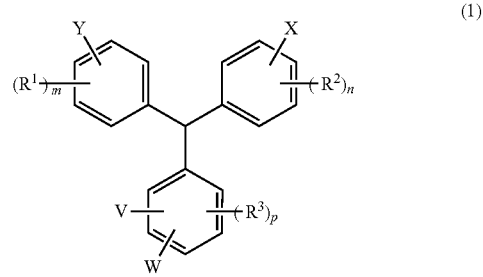

(1)

in the formula, $R^1$, $R^2$, and $R^3$ are each independently an alkyl group having 1 to 8 carbon atoms, m and n are each independently an integer of 1 to 4, p is an integer of 0 to 4, V is a hydrogen atom, a (meth)acryloyloxy group, or a hydroxyl group, and W, X, and Y are each independently a (meth)acryloyloxy group or a hydroxyl group, wherein the average number of (meth)acryloyloxy groups per molecule is in a range of 0.5 to 2.5, wherein at least one hydroxyl group is not in the ortho-position with respect to the center.

2. The phenolic hydroxyl group-containing composition according to claim 1, wherein the phenolic hydroxyl group-containing compounds have a molecular structure represented by general formula (2) below,

[Chem. 2]

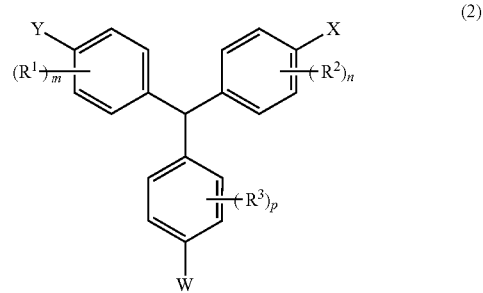

(2)

in the formula, $R^1$, $R^2$, and $R^3$ are each independently an alkyl group having 1 to 8 carbon atoms, m and n are each independently an integer of 1 to 4, p is an integer of 0 to 4, and W, X, and Y are each independently a (meth)acryloyloxy group or a hydroxyl group, wherein at least one of W, X, and Y is a hydroxyl group, and at least one of W, X, and Y is a (meth)acryloyloxy group.

3. The phenolic hydroxyl group-containing composition according to claim 1, wherein the phenolic hydroxyl group-containing compounds are produced by reacting a phenolic hydroxyl group-containing aromatic aldehyde (a2) with a (meth)acrylic acid halide (β) to produce a reaction product (γ) represented by general formula (4) below,

[Chem. 3]

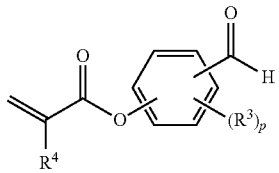

(4)

in the formula, $R^3$ is an alkyl group having 1 to 8 carbon atoms, p is an integer of 0 to 4, and $R^4$ is a hydrogen atom of a methyl group), and then polycondensing the reaction product (γ) with an alkyl-substituted phenol (a1).

4. A (meth)acryloyl group-containing resin produced by reacting a phenolic hydroxyl group-containing composition with an aldehyde compound, the phenolic hydroxyl group-containing composition containing a plurality of phenolic hydroxyl group-containing compounds represented by the general formula (1) below,

[Chem. 4]

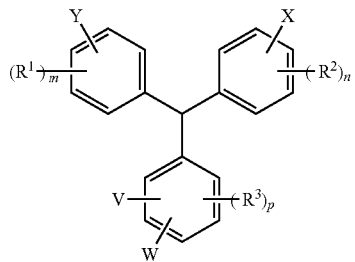

(1)

in the formula, $R^1$, $R^2$, and $R^3$ are each independently an alkyl group having 1 to 8 carbon atoms, m and n are each independently an integer of 1 to 4, p is an integer of 0 to 4, V is a hydrogen atom, a (meth)acryloyloxy group, or a hydroxyl group, and W, X, and Y are each independently a (meth)acryloyloxy group or a hydroxyl group, wherein the average number of (meth)acryloyloxy groups per molecule is in a range of 0.5 to 2.5, wherein at least one hydroxyl group is not in the ortho-position with respect to the center.

5. The (meth)acryloyl group-containing resin according to claim 4, wherein the phenolic hydroxyl group-containing compounds have a molecular structure represented by general formula (2) below,

[Chem. 5]

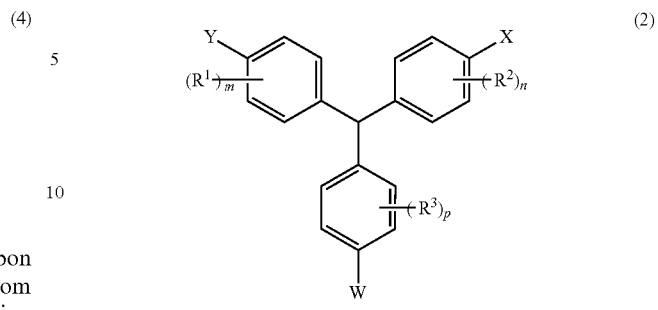

(2)

in the formula, $R^1$, $R^2$, and $R^3$ are each independently an alkyl group having 1 to 8 carbon atoms, m and n are each independently an integer of 1 to 4, p is an integer of 0 to 4, and W, X, and Y are each independently a (meth)acryloyloxy group or a hydroxyl group, wherein at least one of W, X, and Y is a hydroxyl group, and at least one of W, X, and Y is a (meth)acryloyloxy group.

6. The (meth)acryloyl group-containing resin according to claim 4, wherein the phenolic hydroxyl group-containing compounds are produced by reacting a phenolic hydroxyl group-containing aromatic aldehyde (a2) with a (meth)acrylic acid halide (β) to produce a reaction product (γ) represented by general formula (4) below,

[Chem. 6]

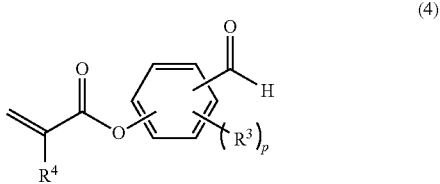

(4)

in the formula, $R^3$ is an alkyl group having 1 to 8 carbon atoms, p is an integer of 0 to 4, and $R^4$ is a hydrogen atom of a methyl group), and then polycondensing the reaction product (γ) with an alkyl-substituted phenol (a1).

7. A curable composition comprising the (meth)acryloyl group-containing resin according to claim 4.

8. A cured product produced by polymerizing the curable composition according to claim 7.

9. A resist material comprising the curable composition according to claim 7.

* * * * *